United States Patent [19]

Pascual

[11] Patent Number: 5,077,304
[45] Date of Patent: Dec. 31, 1991

[54] AMINOPYRIDINES

[75] Inventor: Alfons Pascual, Basel, Switzerland

[73] Assignee: Ciba-Geigy Corporation, Ardsley, N.Y.

[21] Appl. No.: 547,649

[22] Filed: Jul. 2, 1990

[30] Foreign Application Priority Data

Jul. 7, 1989 [CH] Switzerland ............... 2533/89

[51] Int. Cl.$^5$ ............... A01N 43/40; C07D 213/16; C07D 213/72
[52] U.S. Cl. ............... 514/346; 514/349; 514/352; 514/353; 546/292; 546/297; 546/305; 546/306
[58] Field of Search ............... 546/292, 297, 305, 306; 514/346, 349, 352, 353

[56] References Cited

U.S. PATENT DOCUMENTS

| | | | |
|---|---|---|---|
| 4,328,247 | 5/1982 | Drabek et al. | 514/637 |
| 4,812,466 | 3/1989 | Boger et al. | 514/351 |
| 4,866,079 | 9/1989 | Boger et al. | 514/346 |

*Primary Examiner*—Mary C. Lee
*Assistant Examiner*—Joseph K. McKane
*Attorney, Agent, or Firm*—Kevin T. Mansfield; Edward McC.Roberts

[57] ABSTRACT

Novel 3-amino-2,4-dialkylpyridine derivatives

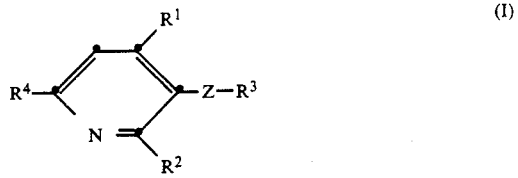

(I)

in which $R^1$ and $R^2$ are each independently $C_1-C_6$alkyl, $R^3$ is $C_1-C_{12}$alkyl, $C_3-C_6$cycloalkyl, $C_1-C_4$alkyl substituted by $C_3-C_6$cycloalkyl, or $C_3-C_6$ cycloalkyl substituted by $C_1-C_4$alkyl, $R^4$ is hydrogen, halogen, $C_1-C_6$alkyl, phenoxy, or phenoxy that is mono- or di-substituted by halogen, $C_1-C_4$alkyl, $C_1-C_4$ alkoxy, $C_1-C_4$alkylthio, $C_1-C_4$alkylamino, di-$C_1-C_4$alkylamino, $C_1-C_4$alkylcarbonylamino, $C_1-C_4$alkylcarbonyl, benzoyl, nitro, cyano, $C_1-C_4$alkoxycarbonyl, $C_1-C_4$haloalkyl or by $C_1-C_4$haloalkoxy, and Z is a bridge member —NH—C-S—NH—, —N═C(SR$^5$)—NH— or —N═C═N— wherein $R^5$ is $C_1-C_6$alkyl or $C_3-C_5$alkenyl, can be used as pesticides. Preferably, insects and arachnids can be controlled.

13 Claims, No Drawings

AMINOPYRIDINES

The present invention relates to novel 3-amino-2,4-dialkylpyridine derivatives, to processes and intermediates for their preparation, to pesticidal compositions containing those compounds, and to their use in controlling pests.

The 3-amino-2,4-dialkylpyridines according to the invention correspond to formula I

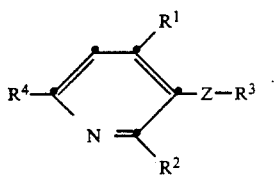

(I)

in which $R^1$ and $R^2$ are each independently $C_1$–$C_6$alkyl, $R^3$ is $C_1$–$C_{12}$alkyl, $C_3$–$C_6$cycloalkyl, $C_1$–$C_4$alkyl substituted by $C_3$–$C_6$cycloalkyl, or $C_3$–$C_6$cycloalkyl substituted by $C_1$–$C_4$alkyl, $R^4$ is hydrogen, halogen, $C_1$–$C_6$-alkyl, phenoxy, or phenoxy that is mono- or di-substituted by halogen, $C_1$–$C_4$alkyl, $C_1$–$C_4$alkoxy, $C_1$–$C_4$alkylthio, $C_1$–$C_4$alkylamino, di-$C_1$–$C_4$alkylamino, $C_1$–$C_4$alkylocarbonylamino, $C_1$–$C_4$alkylcarbonyl, benzoyl, nitro, cyano, $C_1$–$C_4$alkoxycarbonyl, $C_1$–$C_4$haloalkyl or by $C_1$–$C_4$haloalkoxy, and Z is a bridge member -NH-CS-NH-, -N=C($SR^5$)-NH- or -N=C=N- wherein $R^5$ is $C_1$–$C_6$alkyl or $C_3$–$C_5$alkenyl.

As a class, pyridylguanidines are known from the literature from DE-OS 2 557 438 to be pharmaceutically active anti-hypertensives. Pyridylcarbodiimides are described as intermediates for the preparation of those active substances.

The individual generic terms used in the definition of formula I according to the invention are to be understood as follows:

The halogen atoms suitable as substituents are both fluorine and chlorine atoms as well as bromine and iodine atoms, with fluorine and chlorine being preferred. Halogen in such cases is either an independent substituent or part of a substituent as in haloalkyl or haloalkoxy.

The alkyl, alkylthio and alkoxy radicals suitable as substituents may be straight-chain or branched. There may be mentioned as examples of such alkyl radicals methyl, ethyl, propyl, isopropyl, butyl, i-butyl, sec.butyl, tert.-butyl or pentyl, hexyl, octyl and their isomers. Suitable alkoxy radicals are, inter alia: methoxy, ethoxy, propoxy, isopropoxy or butoxy and their isomers. Alkylthio is, for example, methylthio, ethylthio, isopropylthio, propylthio or the isomers of butylthio.

If the alkyl, alkoxy or phenyl radicals suitable as substituents are halo-substituted, then they may be only partially halogenated or alternatively perhalogenated. The above definitions for the halogen atoms, alkyl and alkoxy apply here. Examples of the alkyl elements of these groups are: methyl mono- to tri-substituted by fluorine, chlorine and/or bromine, such as, for example, $CHF_2$ or $CF_3$; ethyl mono- to penta-substituted by fluorine, chlorine and/or bromine, such as, for example, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl each mono- to hepta-substituted by fluorine, chlorine and/or bromine, such as, for example, $CH_2CHBrCH_2Br$, $CF_2CHFCF_3$, $CH_2CF_2CF_3$ or $CH(CF_3)_2$; butyl or an isomer thereof each mono- to nona-substituted by fluorine, chlorine and/or bromine, such as, for example, $CF(CF_3)CHFCF_3$ or $CH_2(CF_2)_2CF_3$.

Cycloalkyl radicals suitable as substituents are, for example, cyclopropyl, cyclobutyl, cyclopentyl and cyclohexyl.

Examples of alkoxycarbonyl and alkylcarbonyl radicals are methoxycarbonyl, ethoxycarbonyl, propoxycarbonyl, isopropoxycarbonyl and butoxycarbonyl. Alkylcarbonyl is, for example, acetyl, propionyl, butyryl or valeryl, or an isomer thereof.

Of the compounds of formula I, attention is drawn to those sub-groups in which a) $R^1$ and $R^2$ have the same meaning, or
b) $R^3$ is branched $C_3$–$C_5$alkyl, or
c) $R^4$ is phenoxy substituted by halogen, by $C_1$–$C_4$alkyl or by $C_1$–$C_4$alkoxy, or
d) $R^5$ is $C_1$–$C_4$alkyl.

Preferred compounds of sub-group a) are those in which $R^1$ and $R^2$ are isopropyl; preferred compounds of sub-group b) are those in which $R^3$ is isopropyl, tert.-butyl or 1,1-dimethylpropyl; and preferred compounds of sub-group c) are those in which $R^4$ is chlorophenoxy, fluorophenoxy, methoxyphenoxy, tert.-butylphenoxy or dichlorophenoxy.

An especially preferred sub-group of compounds of formula I is that in which $R^1$ and $R^2$ have the same meaning, $R^3$ is branched $C_3$–$C_5$alkyl and $R^4$ is phenoxy substituted by halogen, by $C_1$–$C_4$alkyl, by di-$C_1$–$C_4$alkylamino or by $C_1$–$C_4$alkoxy.

Owing to their advantageous activity against pests, attention is drawn most especially to the group of compounds of formula I in which $R^1$ and $R^2$ are isopropyl, $R^3$ is isopropyl, tert.-butyl or 1,1-dimethylpropyl and $R^4$ is chlorophenoxy, fluorophenoxy, dichlorophenoxy, methoxyphenoxy or tert.-butylphenoxy.

The following may be mentioned as preferred individual compounds of formula I:

1-tert.-butyl-3-[2,4-diisopropyl-6-(4-chlorophenoxy)-pyrid-3-yl]-thiourea, 1-tert.-butyl-3-[2,4-diisopropyl-6-(4-chlorophenoxy)-pyride-3-yl]-S-methyl-isothiourea, 1-tert.-butyl-3-[2,4-diisopropyl-6-(4-chlorophenoxy)-pyrid-3-yl]-carbodiimide, 1-tert.-butyl-3-[2,4-diisopropyl-6-(4-methoxyphenoxy)-pyrid-3-yl]-thiourea, 1-tert.-butyl-3-[2,4-diisopropyl-6-(4-methoxyphenoxy)-pyrid-3-yl]-S-methyl-isothiourea and 1-tert.-butyl-3-[2,4-diisopropyl-6-(4-methoxyphenoxy)-pyrid-3-yl]-carbodiimide.

The compounds of formula I in which Z-$R^3$ is -N=C($SR^5$)-NH-$R^3$ may exist in the two tautomeric forms

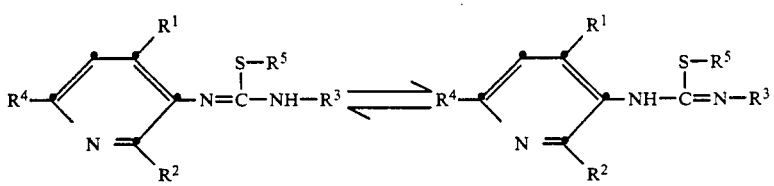

The invention relates both to the individual tautomers and to tautomeric mixtures.

The compounds of formula I according to the invention can be prepared analogously to known processes. A compound of formula I is obtained, for example, by a) reacting an isothiocyanate of formula II

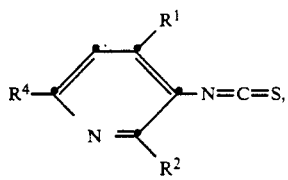 (II)

in which $R^1$, $R^2$ and $R^4$ are as defined for formula I, with a primary amine of formula III $H_2N\text{-}R^3$ (III)

in which $R^3$ is as defined for formula I, to form the thiourea of formula Ia

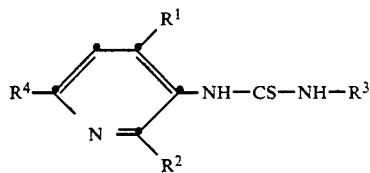 (Ia)

and, if desired, either b) reacting the resulting thiourea of formula Ia with an alkylating agent of formula IV

Y-$R^5$ (IV)

in which $R^5$ is as defined for formula I and Y is a leaving group, to form the isothiourea of formula Ib

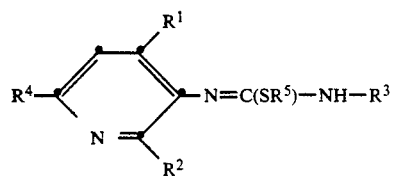 (Ib)

or c) converting the resulting thiourea of formula Ia into the carbodiimide of formula Ic

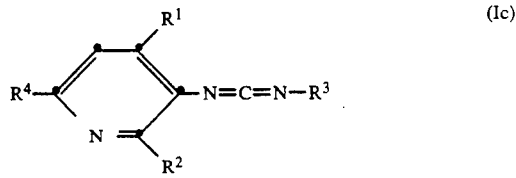 (Ic)

by the removal of hydrogen sulfide.

Process a) is customarily carried out under normal pressure and in the presence of an organic solvent or diluent. The temperature is from 0° C. to +150° C., preferably from +10° C. to +70° C. Suitable solvents or diluents are, for example, ethers and ethereal compounds, such as diethyl ether, dipropyl ether, dibutyl ether, dioxan, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride or chlorobenzene; nitriles, such as acetonitrile or propionitrile; ketones, such as acetone, methyl ethyl ketone, methyl isopropyl ketone, methyl isobutyl ketone or cyclohexanone.

Process b) is advantageously carried out in an inert organic solvent and under normal or slightly elevated pressure. The temperature is from +10° C. to +250° C., and is preferably the boiling temperature of the solvent used or from +50° C. to +150° C. Suitable solvents or diluents are, for example, ethers and ethereal compounds, such as diethyl ether, diisopropyl ether, dioxan or tetrahydrofuran; aromatic hydrocarbons, such as benzene, toluene or xylenes; ketones, such as acetone, methyl ethyl ketone or cyclohexanone, alcohols or dimethylformamide.

Process c) is advantageously carried out under normal pressure in an aprotic organic solvent or diluent. The temperature is from 0° C. to +150° C., preferably from +10° C. to +50° C. Suitable solvents or diluents are, for example, ethers and ethereal compounds, such as diethyl ether, dipropyl ether, dibutyl ether, dioxan, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride or chlorobenzene; nitriles, such as acetonitrile or propionitrile; ketones, such as acetone, methyl ethyl ketone, methyl isopropyl ketone or cyclohexanone. The hydrogen sulfide is removed according to procedures described in the literature (Chemistry Letters 1977, p. 575-576; Tetrahedron Letters 1985, p. 1661-1664; Ber. Dtsch. Chem. Ges. 6, 1873, p. 1398; Bull. Soc. Chim. 1956. p. 1360). The reagents used for the removal are, inter alia, HgO, certain pyridinium salts, chloroacetic acid esters, cyanuric acid chloride, p-toluenesulfonic acid chloride or certain phosphoric acid ester derivatives.

The isothiocyanates of formula II can be prepared according to methods known in principle by reacting a 3-aminopyridine of formula V

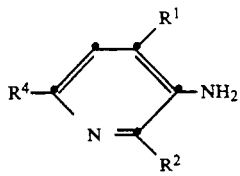
(V)

in which $R^1$, $R^2$ and $R^4$ are as defined for formula I either
a) with carbon disulfide in the presence of a tertiary amine in pyridine, and treating the reaction product with N,N'-dicyclohexylcarbodiimide in pyridine, as in the process described in Chem. Ber. 101. 1746 (1968), or
b) with carbon disulfide in the presence of a tertiary amine, methylating the reaction product with a methylating agent, such as methyl iodide or dimethyl sulfate, and thermolysing at a temperature of from +80° C. to 250° C., especially from +120° C. to +160° C., such as, for example, at +140° C., as in the process described in J. Chem. Soc. 1956, 1644.

The tertiary amines suitable for use in large-scale synthesis are preferably those that can simultaneously act as solvents, such as triethylamine and pyridine. On a laboratory scale, however, tertiary amines such as 1,5-diazabicyclo[4.3.0]non-5-ene or 1,8-diazabicyclo[5.4.0]undec-7-ene are also suitable.

The 3-aminopyridines of formula V can also be obtained according to processes that are known per se. The 3-aminopyridines of formula V are obtained in a particularly simple manner by the catalytic reduction with hydrogen of a 3-nitropyridine of formula VI

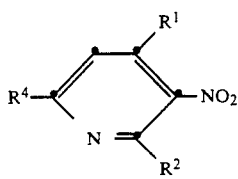
(VI)

in which $R^1$, $R^2$ and $R^4$ are as defined for formula I.

The catalytic reduction is carried out in customary manner by reaction with gaseous hydrogen in the presence of a suitable catalyst, advantageously in an inert solvent. The reduction can be performed under either normal pressure or an elevated pressure of up to 20 bar. The reaction temperatures are from +10° C. to +40° C.

Suitable catalysts are platinum, palladium or nickel catalysts, such as platinum, platinum black, platinum/BaSO$_4$, palladium, palladium/carbon or Raney nickel. Alcohols, such as methanol, ethanol or isopropanol, carboxylic acid esters, such as ethyl acetate, or ethers, such as diethyl ether, tetrahydrofuran or dioxan, may be used as solvents. In the case where $R^4$ is halogen, by suitable choice of the reaction conditions for the reduction either the 3-aminopyridine can be obtained with retention of the 6-halogen atom or, in the same reaction step, the halogen atom can be removed to yield those 3-aminopyridines of formula V in which $R^4$ is hydrogen.

The 3-nitropyridines of formula VI in which R is chlorine or bromine are obtained by reacting 6-hydroxy-3-nitropyridines of formula VII

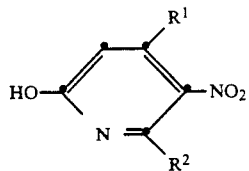
(VII)

in which $R^1$ and $R^2$ are as defined for formula I, with chlorinating or brominating agents, such as phosphorus pentachloride or phosphorus pentabromide. From the so-obtained 6-chloro- or 6-bromo-3-nitropyridines of sub-formula VIa

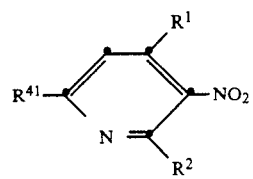
(VIa)

in which $R^1$ and $R^2$ are as defined for formula I and $R^{41}$ is chlorine or bromine, the 6-phenoxy-3-nitropyridines of sub-formula VIb

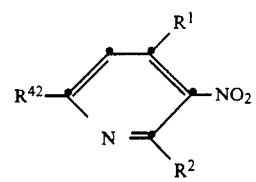
(VIb)

in which $R^1$ and $R^2$ are as defined for formula I and $R^{42}$ is phenoxy, or phenoxy that is mono- or di-substituted by halogen, $C_1$–$C_4$alkyl, $C_1$–$C_4$alkoxy, $C_1$–$C_4$alkylthio, $C_1$–$C_4$alkylamino, di-$C_1$–$C_4$alkylamino, $C_1$–$C_4$alkylaminocarbonyl, $C_1$–$C_4$alkylcarbonyl, benzoyl, nitro, cyano, $C_1$–$C_4$alkoxycarbonyl, $C_1$–$C_4$haloalkyl or by $C_1$–$C_4$haloalkoxy, are obtained by reacting the compound VIa with a phenol of formula VIII $$R^{42}\text{-H} \qquad (VIII)$$

in the presence of a strong base.

The substitution reaction (vIa→VIb) can be carried out under conventional phase transfer conditions in a two-phase reaction medium or in a single-phase reaction. In a typical phase transfer process the reactants VIa and vIII are dissolved in an aromatic solvent, such as benzene, toluene or xylene, and a phase transfer catalyst, such as, for example, 18-crown-6, tetrabutylammonium chloride or triethylbutylammonium chloride, is added, and a concentrated aqueous alkali hydroxide solution, for example 50% sodium hydroxide solution, is added as the second phase. The reaction temperatures are from +20° C. to the boiling point of the mixture. In the case of a single-phase reaction procedure, VIa, VIII and alkali base are dissolved in a polar solvent, such as dimethyl sulfoxide, dimethylformamide, methanol, ethanol or isopropanol, and heated preferably to boiling point.

The 6-hydroxy-3-nitropyridines of formula VII can be prepared analogously to the following reaction scheme.

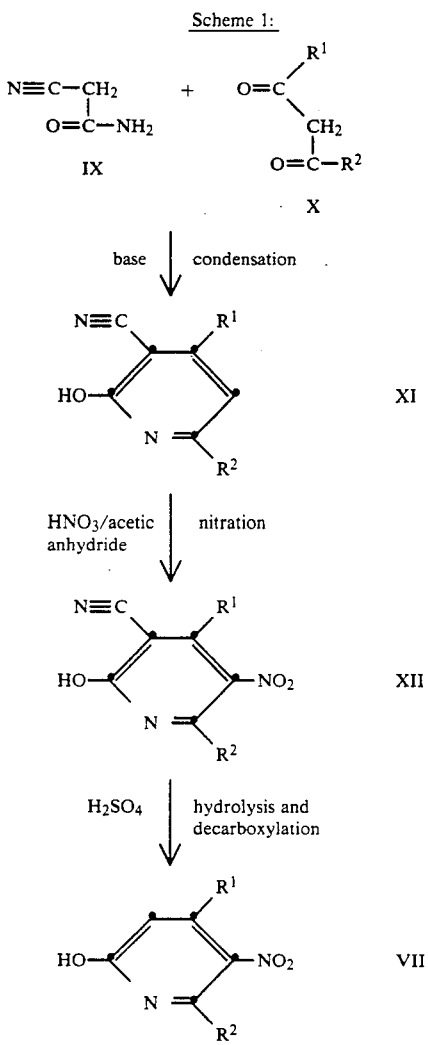

$R^1$ and $R^2$ are as defined for formula I. The reaction conditions and reagents are selected as in analogous process steps known from the literature.

The intermediates of formula II are novel. They have been developed specifically for the synthesis of the compounds of formula I. The present invention therefore also extends to those intermediates. The intermediates of formulae V and VI, with the exception of the two individual compounds in which $R^1$, $R^2$ and $R^4$ are each methyl, are also novel, and the invention also extends to those novel intermediates.

The intermediates of formulae III, IV and VIII are mostly known and are available commercially, or can be prepared according to known methods.

It has been found that whilst being well tolerated by warm-blooded animals, fish and plants, the compounds of formula I of the invention are valuable active ingredients in the control of pests. In particular, the use of the active ingredients of the invention is directed to insects and spinning organisms that occur in useful plants and ornamentals in agriculture, especially in cotton, vegetable and fruit plantations, in forestry, in stock and material protection and also in the hygiene sector especially in connection with domestic animals and productive livestock. They are effective against all or individual stages of development of normally sensitive species and also resistant species. Their effect may manifest itself in a direct kill of the pests, or not until after some time, for example during shedding, or in a reduced oviposition and/or hatching rate. The following are included among the above-mentioned pests: of the order Lepidoptera, for example Acleris spp., Adoxophyes spp., Aegeria spp., Agrotis spp., *Alabama argillaceae,* Amylois spp., *Anticarsia gemmatalis,* Archips spp., Argyrotaenia spp., Autographa spp., *Busseola fusca, Cadra cautella, Carposina nipponensis,* Chilo spp., Choristoneura spp., *Clysia ambiguella,* Cnaphalocrocis spp., Cnephasia spp., Cochylis spp., Coleophora spp., *Crocidolomia binotalis, Cryptophlebia leucotreta,* Cydia spp., Diatraea spp., *Diparopsis castanea,* Earias spp., Ephestia spp., Eucosma spp., *Eupoecilia ambiuella,* Euproctis spp., Euxoa spp., Grapholita spp., *Hedya nubiferana,* Heliothis spp., *Hellula undalis, Hyphantria cunea, Keiferia lycopersicella, Leucoptera scitella,* Lithocollethis spp., *Lobesia botrana,* Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,* Pieris spp., *Plutella xylostella,* Prays, spp., Scirpophaga spp., Sesamia spp., Sparganothis spp., Spodoptera spp., Synanthedon spp., Thaumetopoea spp., Trichoplusia ni and Yponomeuta spp.; of the order Coleoptera. for example Agriotes spp., Anthonomus spp., *Atomaria linearis, Chaetocnema tibialis,* Cosmopolites spp., Curculio spp., Dermestes spp., Diabrotica spp., Epilachna spp., Eremnus spp., *Leptinotarsa decemlineata,* Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.; of the order Orthoptera, for example Blatta spp., Blattella spp., Gryllotalpa spp., *Leucophaea maderae,* Locusta spp., Periplaneta spp. and Schistocerca spp.; of the order Isoptera, for example Reticulitermes spp.; of the order Psocoptera, for example Liposcelis spp.; of the order Anoplura, for example Haematopinus spp., Linognathus spp., Pediculus spp., Pemphigus spp. and Phylloxera spp.; of the order Mallophaga, for example Damalinea spp. and Trichodectes spp.; of the order Thysanoptera, for example Frankliniella spp., Hercinothrips spp., Taeniothrips spp., *Thrips palmi, Thrips tabaci* and *Scirtothrips aurantii;* of the order Heteroptera, for example Cimex spp., *Distantiella theobroma,* Dysdercus spp., Euchistus spp., Eurygaster spp., Leptocorisa spp., Nezara spp., Piesma spp., Rhodnius spp., *Sahlbergella singularis,* Scotinophara spp. and Triatoma spp.; of the order Homoptera, for example *Aleurothrixus floccosus, Aleyrodes brassicae,* Aonidiella spp., Aphididae, Aphis spp., Aspidiotus spp., Bemisia tabaci, Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* of the order Hymenoptera, for example Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.; of the order Diptera, for example Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami,* Phorbia spp., *Rhagoletis pomonella,* Sciara spp., Stomoxys spp., Tabanus spp., Tannia spp. and Tipula spp.; of the order Siphonaptera, for example Ceratophyllus spp., *Xenopsylla cheopis,* of the order Acarina, for example *Acarus siro, Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp.; and of the order Thysanura, for example *Lepisma saccharina.*

The good pesticidal activity of the compounds of formula I of the invention corresponds to a death rate (mortality) of at least 50-60% of the pests mentioned.

The activity of the compounds of the invention and of the compositions containing them can be substantially broadened and adapted to the prevailing circumstances by the addition of other insecticides and/or acaricides. Examples of suitable additives are representatives of the following classes of active substances: organophosphorus compounds, nitrophenols and derivatives thereof, formamidines, ureas, carbamates, pyrethroids, chlorinated hydrocarbons and Bacillus thuringiensis preparations.

The compounds of formula I are used in unmodified form or, preferably, together with the adjuvants conventionally employed in the art of formulation, and can therefore be formulated in known manner e.g. into emulsifiable concentrates, directly sprayable or dilutable solutions, dilute emulsions, wettable powders, soluble powders, dusts, granulates, and also encapsulations in polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations of those compounds with other insecticides or acaricides and, if desired, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, e.g. especially dolomite or pulverised plant residues.

Depending on the nature of the compound of formula I to be formulated or of the combinations of those compounds with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tall oil. Mention may also be made of fatty acid methyltaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfaeed and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenol-polyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one Cs-Czzalkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyl-di-(2-chloroethyl)-ethylammonium bromide.

The surfactants customarily used in the art of formulation are described, inter alia, in the following publications:

"1985 International Mc Cutcheon's Emulsifiers & Detergents", Glen Rock N.J. USA, 1985", H. Stache, "Tensid-Taschenbuch", 2nd edition, C. Hanser Verlag Munich, Vienna 1981, M. and J. Ash "Encyclopedia of Surfactants", vol. I-III, Chemical Publishing Co., New York, 1980-1981.

The pesticidal compositions usually contain 0.1 to 99%, especially 0.1 to 95%, of a compound of formula I or combinations of that compound with other insecticides or acaricides, 1 to 99.9% of a solid or liquid adjuvant and 0 to 25%, preferably 0.1 to 20%, of a surfactant. Whereas commercial products will preferably be formulated as concentrates, the end user will normally employ dilute formulations that contain substantially lower concentrations of active ingredient. Typical concentrations are from 0.1 to 1000 ppm, preferably from 0.1 to 500 ppm. The rate of application per hectare is generally from 1 to 1000 g of active ingredient per hectare, preferably from 25 to 500 g/ha.

The preferred formulations are composed especially as follows: (throughout percentages are by weight)
Emulsifiable concentrates
  active ingredient: 1 to 20%, preferably 5 to 10%
  surfactant: 5 to 30%, preferably 10 to 20%
  liquid carrier: 50 to 94%, preferably 70 to 85%
Dusts
  active ingredient: 0.1 to 10%, preferably 0.1 to 1%
  solid carrier: 99.9 to 90%, preferably 99.9 to 99%
Suspension concentrates
  active ingredient: 5 to 75%, preferably 10 to 50%
  water: 94 to 24%, preferably 88 to 30%
  surfactant: 1 to 40%, preferably 2 to 30%
Wettable powders
  active ingredient: 0.5 to 90%, preferably 1 to 80%
  surfactant: 0.5 to 20%, preferably 1 to 15%
  solid carrier: 5 to 95%, preferably 15 to 90%
Granulates
  active ingredient: 0.5 to 30%, preferably 3 to 15%
  solid carrier: 99.5 to 70%, preferably 97 to 85%

The compositions may also contain further auxiliaries such as stabilisers, antifoams, preservatives, viscosity regulators, binders, tackifiers as well as fertilisers or other active ingredients for obtaining special effects.

The following Examples serve to illustrate the invention but do not limit the invention.

PREPARATION EXAMPLES

EXAMPLE P1

2,4-diisopropyl-6-(4-chlorophenoxy)-3-nitropyridine

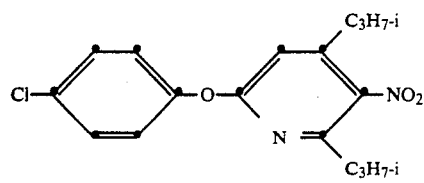

0.77 g of 4-chlorophenol and 1.00 g of potassium carbonate are suspended in 6 ml of dimethyl sulfoxide and the suspension is heated for 1 hour at +60° C.; a solution of 1.46 g of 6-chloro-2,4-diisopropyl-3-nitropyridine in 4 ml of dimethyl sulfoxide is then added dropwise. When the addition is complete, the mixture is heated for 1 hour at +120° C. with vigorous stirring. After cooling, the reaction mixture is poured onto 100 ml of water and 50 ml of toluene and then saturated with sodium chloride. The resulting suspension is filtered over diatomaceous earth and the filtrate is extracted with toluene. The organic phase is dried over magnesium sulfate and the solvent is evaporated. The residue is purified by column chromatography on silica gel (eluant: ethyl acetate/hexane 1:30). 2,4-Diisopropyl-6-(4-chlorophenoxy)-3-nitropyridine is obtained in the form of a light-yellow crystalline powder, m.p. 102°-104° C.

EXAMPLE P2

2,4-diisopropyl-6-(4-chlorophenoxv)-3-aminopyridine

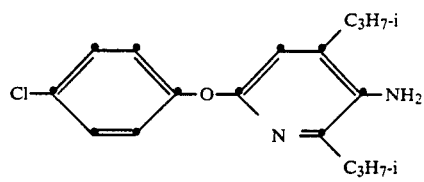

11.9 g of 2,4-diisopropyl-6-(4-chlorophenoxy)-3-nitropyridine are dissolved in 120 ml of tetrahydrofuran and, after the addition of 12 g of Raney nickel (suspended in ethanol), hydrogenated under normal pressure at from +30° C. to +35° C. The reaction mixture is filtered over diatomaceous earth and the filtrate is concentrated. The residue is purified by column chromatography on silica gel (eluant: ethyl acetate/hexane 1:3). 2,4-Diisopropyl-6-(4-chlorophenoxy)-3-aminopyridine is obtained in the form of a light-yellow crystalline powder, m.p. 86°-88° C.

EXAMPLE P3

2,4-diisopropyl-3-aminopyridine

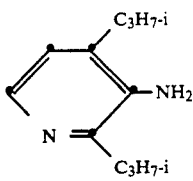

5.0 g of 6-chloro-2,4-diisopropyl-3-nitropyridine are dissolved in 100 ml of tetrahydrofuran and, after the addition of 2.75 g of triethylamine and 7.5 g of 5% palladium/carbon catalyst, hydrogenated under normal pressure at from +20° C. to +25° C. The reaction mixture is filtered over diatomaceous earth and the filtrate is concentrated. The residue is purified by column chromatography on silica gel (eluant: ethyl acetate/hexane 1:3). 2,4-Diisopropyl-3-aminopyridine is obtained in the form of a waxlike solid, m.p. 35°-39° C.

EXAMPLE P4

6-chloro-2,4-diisopropyl-3-aminooyridine

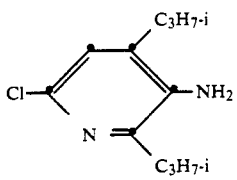

30.0 g of 6-chloro-2,4-diisopropyl-3-nitropyridine are dissolved in 450 ml of tetrahydrofuran and, after the addition of 30.0 g of Raney nickel (suspended in ethanol), hydrogenated under a hydrogen pressure of 20 bar at from +30° C. to +35° C. The reaction mixture is filtered over diatomaceous earth and the filtrate is concentrated. The residue is purified by column chromatography on silica gel (eluant: ethyl acetate/hexane 3). 6-Chloro-2,4-diisopropyl-3-aminopyridine is obtained in the form of a clear crystalline powder, m.p. 53°-56° C.

EXAMPLE P5

2,4-diisopropyl-6-(4-chlorophenoxy)-pyrid-3-ylisothiocyanate

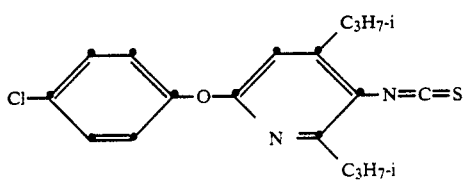

A solution of 5.0 g of triethylamine in 10 ml of pyridine is cooled to from −5° C. to −10° C., and 20 ml of carbon disulfide are added dropwise. At −10° C., a solution of 15.0 g of 2,4-diisopropyl-6-(4-chlorophenoxy)-3-aminopyridine in 27 ml of pyridine is slowly added dropwise. The mixture is further stirred at −10° C. for 1 hour. A solution of 10.0 g of N,N'-dicyclohexylcarbodiimide in 10 ml of pyridine is then added. After a further 3 hours at −10° C., the mixture is stirred for 18 hours at room temperature. The reaction mixture is concentrated by evaporation and hexane is added to the residue. Thehhexane solution is filtered off and concentrated by evaporation. 2,4-Diisopropyl-6-(4-chlorophenoxy)-pyrid-3-yl isothiocyanate is obtained in the form of a yellow oil, which is used for the next reaction without being further purified; IR ($CCl_4$): 2090, 1490, 1220 $cm^{-1}$.

EXAMPLE P6

1-tert.-butyl-3-[2,4-diisopropyl-6-(4-chlorophenoxy)pyrid-3-yl]-thiourea

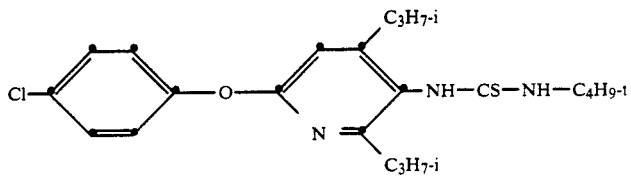

8.15 g of 2,4-diisopropyl-6-(4-chlorophenoxy)-pyrid-3-yl isothiocyanate are diluted with 30 ml of toluene, and 2.0 g of tert.-butylamine are added dropwise. The reaction mixture is then further stirred for 2 hours at approximately +60° C. The reaction mixture is concentrated and hexane is added to the residue. The resulting solid is filtered off and subsequently washed with hexane. 1-tert.-Butyl-3-[2,4-diisopropyl-6-(4-chlorophenoxy)-pyrid-3-yl]-thiourea is obtained in the form of colourless crystals, m.p. 165°-167° C.

EXAMPLE P7

1-tert.-butyl-3-[2,4-diisopropyl-6-(4-chlorophenoxy)pyrid-3-yl-S-methyl-isothiourea

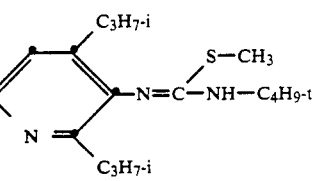

2.0 g of methyl iodide are added at room temperature to 2.50 g of 1-tert.-butyl-3-[2,4-diisopropyl-6-(4-chlorophenoxy)-pyrid-3-yl]-thiourea in 30 ml of ethanol and the mixture is heated at +75° C. for 5 hours. The mixture is then concentrated by evaporation and the residue is taken up in methylene chloride and washed twice with dilute sodium bicarbonate solution. The organic phase is dried over magnesium sulfate and the solvent is evaporated. The crude product is purified by column chromatography on silica gel (eluant: ethyl acetate/hexane 1:3). 1-tert.-Butyl-3-[2,4-diisopropyl-6-(4-chlorophenoxy)-pyrid-3-yl]-S-methyl-isothiourea is obtained in the form of a colourless crystalline powder, m.p. 95°-100° C.

EXAMPLE P8

1-tert.-butyl-3-[2,4-diisopropyl-6-(4-chlorophenoxy)pyrid-3-yl]-carbodiimide

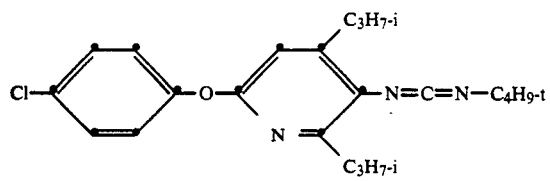

3.0 g of 1-tert.-butyl-3-[2,4-diisopropyl-6-(4-chlorophenoxy)-pyrid-3-yl]-thiourea and 2.1 g of 2-chloro-1-methylpyridinium iodide are placed in 20 ml of acetonitrile and, at room temperature, a solution of 1.6 g of triethylamine in 7 ml of acetonitrile is added. The reaction mixture is then stirred for 1 hour at approximately +65° C. After evaporation of the solvent, the residue is taken up in hexane/water. The organic phase is dried over magnesium sulfate and the solvent is removed in vacuo. The crude product is purified by column chromatography on silica gel (eluant: ethyl acetate/hexane 1:5). 1-tert.-Butyl-3-[2,4-diisopropyl-6-(4-chlorophenoxy)-pyrid-3-yl]-carbodiimide is obtained in the form of a colourless oil which solidifies after a few hours. M.p. 46°-55° C.

The intermediates and the active ingredients of the invention listed in the following Tables 1 to 6 are obtained in an analogous manner.

TABLE 1

| Comp. No. | $R^1$ | $R^2$ | $R^4$ | m.p. [°C.] |
|---|---|---|---|---|
| 1.01 | $C_3H_7$-i | $C_3H_7$-i | 4-Cl—$C_6H_4$—O— | 102-104 |
| 1.02 | $CH_3$ | $CH_3$ | $C_6H_5$—O— | 46-48 |
| 1.03 | $CH_3$ | $CH_3$ | 4-Cl—$C_6H_4$—O— | 56-58 |
| 1.04 | $CH_3$ | $CH_3$ | $C_6H_5$—S— | 94-96 |
| 1.05 | $C_3H_7$-i | $C_3H_7$-i | $C_6H_5$—O— | 67-69 |
| 1.06 | $C_3H_7$-i | $C_3H_7$-i | $C_6H_5$—S— | 59-66 |
| 1.07 | $C_3H_7$-i | $C_3H_7$-i | 4-F—$C_6H_4$—O— | 73-75 |
| 1.08 | $C_3H_7$-i | $C_3H_7$-i | 2-F—$C_6H_4$—O— | 85-87 |
| 1.09 | $C_3H_7$-i | $C_3H_7$-i | 2-Cl-4-Cl—$C_6H_3$—O— | 79-83 |
| 1.10 | $C_3H_7$-i | $C_3H_7$-i | 3-Cl-4-Cl—$C_6H_3$—O— | 58-61 |
| 1.11 | $C_3H_7$-i | $C_3H_7$-i | 4-$CH_3$O—$C_6H_4$—O— | 119-123 |
| 1.12 | $C_3H_7$-i | $C_3H_7$-i | 4-$C_4H_9$-t-$C_6H_4$—O— | 90-92 |
| 1.13 | $C_3H_7$-i | $C_3H_7$-i | 4-$CH_3$CO—$C_6H_4$—O— | 98-100 |
| 1.14 | $C_3H_7$-i | $C_3H_7$-i | 4-$(CH_3)_2$N—$C_6H_4$—O— | 148-152 |
| 1.15 | $C_3H_7$-i | $C_3H_7$-i | 4-$CH_3$CONH—$C_6H_4$—O— | 186-188 |
| 1.16 | $C_2H_5$ | $C_2H_5$ | 4-Cl—$C_6H_4$—O— | 55-58 |
| 1.17 | $C_3H_7$-i | $C_3H_7$-i | 4-$C_6H_5$—CO—$C_6H_4$—O— | 97-98 |
| 1.18 | $C_3H_7$-i | $C_3H_7$-i | 4-$CH_3$S—$C_6H_4$—O— | 106-109 |
| 1.19 | $C_3H_7$-i | $C_3H_7$-i | 4-$CH_3$—$C_6H_4$—O— | 106-108 |
| 1.20 | $C_3H_7$-i | $C_3H_7$-i | 4-CN—$C_6H_4$—O— | |
| 1.21 | $C_3H_7$-i | $C_3H_7$-i | 4-$CF_3$CO—$C_6H_4$—O— | |
| 1.22 | $C_3H_7$-i | $C_3H_7$-i | 4-$CH_3$OCO—$C_6H_4$—O— | |
| 1.23 | $C_3H_7$-i | $C_3H_7$-i | 4-$CF_3$O—$C_6H_4$—O— | |
| 1.24 | $C_2H_5$ | $C_2H_5$ | 4-F—$C_6H_4$—O— | 47-49 |
| 1.25 | $C_2H_5$ | $C_2H_5$ | 2-Cl-4-Cl—$C_6H_3$—O— | |
| 1.26 | $C_2H_5$ | $C_2H_5$ | 3-Cl-4-Cl—$C_6H_3$—O— | |
| 1.27 | $C_3H_7$-i | $C_2H_5$ | $C_6H_5$—O— | |
| 1.28 | $C_3H_7$-i | $C_2H_5$ | 4-Cl—$C_6H_4$—O— | |
| 1.29 | $C_3H_7$-i | $C_2H_5$ | 4-$CH_3$O—$C_6H_4$—O— | |
| 1.30 | $C_2H_5$ | $C_3H_7$-i | $C_6H_5$—O— | |
| 1.31 | $C_2H_5$ | $C_3H_7$-i | 4-Cl—$C_6H_4$—O— | |
| 1.32 | $C_2H_5$ | $C_3H_7$-i | 4-$CH_3$O—$C_6H_4$—O— | |

TABLE 2

| Comp. No. | $R^1$ | $R^2$ | $R^4$ | phys. data |
|---|---|---|---|---|
| 2.01 | $C_3H_7$-i | $C_3H_7$-i | 4-Cl—$C_6H_4$—O— | m.p. 86-88° C. |
| 2.02 | $CH_3$ | $CH_3$ | $C_6H_5$—O— | m.p. 81-85° C. |
| 2.03 | $CH_3$ | $CH_3$ | 4-Cl—$C_6H_4$—O— | m.p. 93-94° C. |
| 2.04 | $CH_3$ | $CH_3$ | $C_6H_5$—S— | m.p. 114-116° C. |
| 2.05 | $C_3H_7$-i | $C_3H_7$-i | $C_6H_5$—O— | m.p. 52-54° C. |
| 2.06 | $C_3H_7$-i | $C_3H_7$-i | $C_6H_5$—S— | $n_D^{25} = 1.6030$ |
| 2.07 | $C_3H_7$-i | $C_3H_7$-i | 4-F—$C_6H_4$—O— | m.p. 50-52° C. |
| 2.08 | $C_3H_7$-i | $C_3H_7$-i | 2-F—$C_6H_4$—O— | $n_D^{24} = 1.5518$ |
| 2.09 | $C_3H_7$-i | $C_3H_7$-i | 2-Cl-4-Cl—$C_6H_3$—O— | $n_D^{24} = 1.5740$ |
| 2.10 | $C_3H_7$-i | $C_3H_7$-i | 3-Cl-4-Cl—$C_6H_3$—O— | $n_D^{24} = 1.5785$ |
| 2.11 | $C_3H_7$-i | $C_3H_7$-i | 4-$CH_3$O—$C_6H_4$—O— | $n_D^{23} = 1.5688$ |
| 2.12 | $C_3H_7$-i | $C_3H_7$-i | 4-$C_4H_9$-t-$C_6H_4$—O— | $n_D^{24} = 1.5517$ |
| 2.13 | $C_3H_7$-i | $C_3H_7$-i | 4-$CH_3$CO—$C_6H_4$—O— | $n_D^{25} = 1.5717$ |
| 2.14 | $C_3H_7$-i | $C_3H_7$-i | 4-$(CH_3)_2$N—$C_6H_4$—O— | m.p. 99-103° C. |
| 2.15 | $C_3H_7$-i | $C_3H_7$-i | 4-$CH_3$CONH—$C_6H_4$—O— | m.p. 120-121° C. |
| 2.16 | $C_2H_5$ | $C_2H_5$ | 4-Cl—$C_6H_4$—O— | $n_D^{21} = 1.5922$ |
| 2.17 | $C_3H_7$-i | $C_3H_7$-i | 4-$C_6H_5$—CO—$C_6H_4$—O— | wax |
| 2.18 | $C_3H_7$-i | $C_3H_7$-i | 4-$CH_3$S—$C_6H_4$—O— | $n_D^{23} = 1.5955$ |
| 2.19 | $C_3H_7$-i | $C_3H_7$-i | 4-$CH_3$—$C_6H_4$—O— | $n_D^{23} = 1.5625$ |
| 2.20 | $C_3H_7$-i | $C_3H_7$-i | 4-CN—$C_6H_4$—O— | |
| 2.21 | $C_3H_7$-i | $C_3H_7$-i | 4-$CF_3$CO—$C_6H_4$—O— | |
| 2.22 | $C_3H_7$-i | $C_3H_7$-i | 4-$CH_3$OCO—$C_6H_4$—O— | |
| 2.23 | $C_3H_7$-i | $C_3H_7$-i | 4-$CF_3$O—$C_6H_4$—O— | |
| 2.24 | $C_2H_5$ | $C_2H_5$ | 4-F—$C_6H_4$—O— | $n_D^{21} = 1.5697$ |

TABLE 2-continued

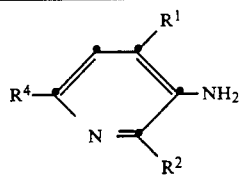

| Comp. No. | $R^1$ | $R^2$ | $R^4$ | phys. data |
|---|---|---|---|---|
| 2.25 | $C_2H_5$ | $C_2H_5$ | 2-Cl-4-Cl—$C_6H_3$—O— | |
| 2.26 | $C_2H_5$ | $C_2H_5$ | 3-Cl-4-Cl—$C_6H_3$—O— | |
| 2.27 | $C_3H_7$-i | $C_2H_5$ | $C_6H_5$—O— | |
| 2.28 | $C_3H_7$-i | $C_2H_5$ | 4-Cl—$C_6H_4$—O— | |
| 2.29 | $C_3H_7$-i | $C_2H_5$ | 4-$CH_3O$—$C_6H_4$—O— | |
| 2.30 | $C_2H_5$ | $C_3H_7$-i | $C_6H_5$—O— | |
| 2.31 | $C_2H_5$ | $C_3H_7$-i | 4-Cl—$C_6H_4$—O— | |
| 2.32 | $C_2H_5$ | $C_3H_7$-i | 4-$CH_3O$—$C_6H_4$—O— | |
| 2.33 | $C_3H_7$-i | $C_3H_7$-i | H | m.p. 35–39° C. |
| 2.34 | $C_3H_7$-i | $C_3H_7$-i | Cl | m.p. 53–56° C. |

TABLE 3

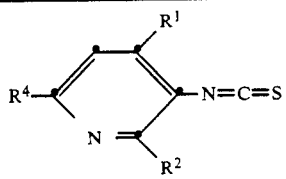

| Comp. No. | $R^1$ | $R^2$ | $R^4$ | phys. data |
|---|---|---|---|---|
| 3.01 | $C_3H_7$-i | $C_3H_7$-i | 4-Cl—$C_6H_4$—O— | oil, IR($CCl_4$): 2090, 1490, 1220 cm$^{-1}$ |
| 3.02 | $CH_3$ | $CH_3$ | $CH_3$ | b.p. 95–100/1 mbar |
| 3.03 | $CH_3$ | $CH_3$ | $C_6H_5$—O— | oil, IR($CCl_4$): 2090, 1345, 1215 cm$^{-1}$ |
| 3.04 | $CH_3$ | $CH_3$ | 4-Cl—$C_6H_4$—O— | oil, IR($CCl_4$): 2120, 2080, 1490, 1345, 1220 cm$^{-1}$ |
| 3.05 | $CH_3$ | $CH_3$ | $C_6H_5$—S— | wax, IR($CCl_4$): 935, 1445, 2080, 2120 cm$^{-1}$ |
| 3.06 | $C_3H_7$-i | $C_3H_7$-i | H | oil, $^1$H-NMR($CDCl_3$, 60 MHz): 8.30, 6.95 dd(J=5 Hz) |
| 3.07 | $C_3H_7$-i | $C_3H_7$-i | Cl | m.p. 56–74° C. |
| 3.08 | $C_3H_7$-i | $C_3H_7$-i | $C_6H_5$—O— | oil, IR($CCl_4$): 2120, 2090, 1590, 1360, 1210 cm$^{-1}$ |
| 3.09 | $C_3H_7$-i | $C_3H_7$-i | $C_6H_5$—S— | oil, IR($CCl_4$): 2120, 2090, 1570, 935 cm$^{-1}$ |
| 3.10 | $C_3H_7$-i | $C_3H_7$-i | 4-F—$C_6H_4$—O— | oil, IR($CCl_4$): 2120, 2080, 1505, 1200 cm$^{-1}$ |
| 3.11 | $C_3H_7$-i | $C_3H_7$-i | 2-F | oil, IR($CCl_4$): 2120, 2090, 1500, 1265 cm$^{-1}$ |
| 3.12 | $C_3H_7$-i | $C_3H_7$-i | 2-Cl-4-Cl—$C_6H_3$—O— | oil, IR($CCl_4$): 2120, 2090, 1600, 1475 cm$^{-1}$ |
| 3.13 | $C_3H_7$-i | $C_3H_7$-i | 3-Cl-4-Cl—$C_6H_3$—O— | oil, IR($CCl_4$): 2120, 2090, 1585, 1470 cm$^{-1}$ |
| 3.14 | $C_3H_7$-i | $C_3H_7$-i | 4-$CH_3O$—$C_6H_4$—O— | oil, IR($CCl_4$): 2120, 2090, 1505, 1205 cm$^{-1}$ |
| 3.15 | $C_3H_7$-i | $C_3H_7$-i | 4-$C_4H_9$-t-$C_6H_4$—O— | oil, IR($CCl_4$): 2120, 2090, 1510, 1220 cm$^{-1}$ |
| 3.16 | $C_3H_7$-i | $C_3H_7$-i | 4-$CH_3CO$—$C_6H_4$—O— | oil, IR($CCl_4$): 2120, 2080, 1690, 1590, 1225 cm$^{-1}$ |
| 3.17 | $C_3H_7$-i | $C_3H_7$-i | 4-$(CH_3)_2N$—$C_6H_4$—O— | m.p. 49–61° C. |
| 3.18 | $C_3H_7$-i | $C_3H_7$-i | 4-$CH_3CONH$—$C_6H_4$—O— | m.p. 122–132° C. |
| 3.19 | $C_3H_7$-i | $C_3H_7$-i | 4-$C_6H_5CO$—$C_6H_4$—O— | m.p. 106–107° C. |
| 3.20 | $C_3H_7$-i | $C_3H_7$-i | 4-$CH_3S$—$C_6H_4$—O— | oil, IR($CCl_4$): 2110, 2090, 1590, 1490, |

TABLE 3-continued

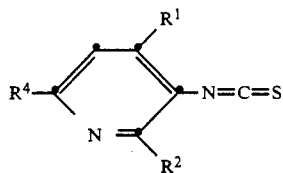

| Comp. No. | R¹ | R² | R⁴ | phys. data |
|---|---|---|---|---|
| | | | | 1215 cm⁻¹ |
| 3.21 | $C_3H_7$-i | $C_3H_7$-i | 4-$CH_3$—$C_6H_4$—O— | m.p. 64–67° C. |
| 3.22 | $C_3H_7$-i | $C_3H_7$-i | 4-CN—$C_6H_4$—O— | |
| 3.23 | $C_3H_7$-i | $C_3H_7$-i | 4-$CF_3$CO—$C_6H_4$—O— | |
| 3.24 | $C_3H_7$-i | $C_3H_7$-i | 4-$CH_3$OCO—$C_6H_4$—O— | |
| 3.25 | $C_3H_7$-i | $C_3H_7$-i | 2-$CF_3$O—$C_6H_4$—O— | |
| 3.26 | $C_2H_5$ | $C_2H_5$ | 4-Cl—$C_6H_4$—O— | oil, IR($CCl_4$): 2080, 1590, 1485, 1215 cm⁻¹ |
| 3.27 | $C_2H_5$ | $C_2H_5$ | 4-F—$C_6H_4$—O— | oil, IR($CCl_4$): 2080, 1590, 1500, 1195 cm⁻¹ |
| 3.28 | $C_2H_5$ | $C_2H_5$ | 2-Cl-4-Cl—$C_6H_3$—O— | |
| 3.29 | $C_2H_5$ | $C_2H_5$ | 3-Cl-4-Cl—$C_6H_3$—O— | |
| 3.30 | $C_3H_7$-i | $C_2H_5$ | $C_6H_5$—O— | |
| 3.31 | $C_3H_7$-i | $C_2H_5$ | 4-Cl—$C_6H_4$—O— | |
| 3.32 | $C_3H_7$-i | $C_2H_5$ | 4-$CH_3$O—$C_6H_4$—O— | |
| 3.33 | $C_2H_5$ | $C_3H_7$-i | $C_6H_5$—O— | |
| 3.34 | $C_2H_5$ | $C_3H_7$-i | 4-Cl—$C_6H_4$—O— | |
| 3.35 | $C_2H_5$ | $C_3H_7$-i | 4-$CH_3$O—$C_6H_4$—O— | |

TABLE 4

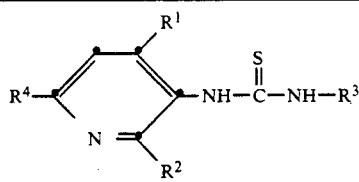

| Comp. No. | R¹ | R² | R³ | R⁴ | m.p. [°C.] |
|---|---|---|---|---|---|
| 4.01 | $C_3H_7$-i | $C_3H_7$-i | $C_4H_9$-t | 4-Cl—$C_6H_4$—O— | 165–167 |
| 4.02 | $CH_3$ | $CH_3$ | $C_4H_9$-t | $CH_3$ | 111–113 |
| 4.03 | $CH_3$ | $CH_3$ | $C_3H_7$-i | $CH_3$ | 151–152 |
| 4.04 | $CH_3$ | $CH_3$ | $C_4H_9$-t | $C_6H_5$—O— | 162–163 |
| 4.05 | $CH_3$ | $CH_3$ | $C_4H_9$-t | 4-Cl—$C_6H_4$—O— | 130–132 |
| 4.06 | $CH_3$ | $CH_3$ | $C_4H_9$-t | $C_6H_5$—S— | 152–154 |
| 4.07 | $C_3H_7$-i | $C_3H_7$-i | $C_4H_9$-t | H | 132–134 |
| 4.08 | $C_3H_7$-i | $C_3H_7$-i | $C_3H_7$-i | H | 155–157 |
| 4.09 | $C_3H_7$-i | $C_3H_7$-i | $C_4H_9$-t | Cl | 144–145 |
| 4.10 | $C_3H_7$-i | $C_3H_7$-i | $C_3H_7$-i | Cl | 214 |
| 4.11 | $C_3H_7$-i | $C_3H_7$-i | $C_4H_9$-t | $C_6H_5$—O— | 142–146 |
| 4.12 | $C_3H_7$-i | $C_3H_7$-i | $C_3H_9$-i | $C_6H_5$—O— | 162–165 |
| 4.13 | $C_3H_7$-i | $C_3H_7$-i | $C_5H_9$-cycl. | $C_6H_5$—O— | 172–178 |
| 4.14 | $C_3H_7$-i | $C_3H_7$-i | $C_4H_9$-t | $C_6H_5$—S— | 114–146 |
| 4.15 | $C_3H_7$-i | $C_3H_7$-i | $C_3H_7$-i | 4-Cl—$C_6H_9$—O— | 156–158 |
| 4.16 | $C_3H_7$-i | $C_3H_7$-i | $C(CH_3)_2$—$C_2H_5$ | 4-Cl—$C_6H_9$—O— | 153–155 |
| 4.17 | $C_3H_7$-i | $C_3H_7$-i | $C_4H_9$-t | 4-F—$C_6H_4$—O— | 156–158 |
| 4.18 | $C_3H_7$-i | $C_3H_7$-i | $C_3H_7$-i | 4-F—$C_6H_4$—O— | 157–160 |
| 4.19 | $C_3H_7$-i | $C_3H_7$-i | $C_4H_9$-t | 2-F—$C_6H_4$—O— | 136–139 |
| 4.20 | $C_3H_7$-i | $C_3H_7$-i | $C_4H_9$-t | 2-Cl-4-Cl—$C_6H_3$—O— | 114–116 |
| 4.21 | $C_3H_7$-i | $C_3H_7$-i | $C_3H_7$-i | 2-Cl-4-Cl—$C_6H_3$—O— | 160–162 |
| 4.22 | $C_3H_7$-i | $C_3H_7$-i | $C_4H_9$-t | 3-Cl-4-Cl—$C_6H_3$—O— | 149–150 |
| 4.23 | $C_3H_7$-i | $C_3H_7$-i | $C_3H_7$-i | 3-Cl-4-Cl—$C_6H_3$—O— | 127–128 |
| 4.24 | $C_3H_7$-i | $C_3H_7$-i | $C_4H_9$-t | 4-$CH_3$O—$C_6H_4$—O— | 169–173 |
| 4.25 | $C_3H_7$-i | $C_3H_7$-i | $C_3H_7$-i | 4-$CH_3$O—$C_6H_4$—O— | 175–180 |
| 4.26 | $C_3H_7$-i | $C_3H_7$-i | $C_4H_9$-t | 4-$C_4H_9$-t-$C_6H_4$—O— | 143–145 |
| 4.27 | $C_3H_7$-i | $C_3H_7$-i | $C_3H_7$-i | 4-$C_4H_9$-t-$C_6H_4$—O— | 161–163 |
| 4.28 | $C_3H_7$-i | $C_3H_7$-i | $C_4H_9$-t | 4-$CH_3$CO—$C_6H_4$—O— | 131–133 |
| 4.29 | $C_3H_7$-i | $C_3H_7$-i | $C_3H_7$-i | 4-$CH_3$CO—$C_6H_4$—O— | 151–154 |
| 4.30 | $C_3H_7$-i | $C_3H_7$-i | $C_4H_9$-t | 4-$(CH_3)_2$N—$C_6H_4$—O— | 154–156 |
| 4.31 | $C_3H_7$-i | $C_3H_7$-i | $C_3H_7$-i | 4-$CH_3$CONH—$C_6H_4$—O— | |
| 4.32 | $C_3H_7$-i | $C_3H_7$-i | $C(CH_3)_2$—$C_2H_5$ | $C_6H_5$—S— | |
| 4.33 | $C_3H_7$-i | $C_3H_7$-i | $C_5H_9$-cycl. | $C_6H_5$—S— | |
| 4.34 | $C_3H_7$-i | $C_3H_7$-i | $CH_2$—$C(CH_3)_3$ | $C_6H_5$—S— | |
| 4.35 | $C_3H_7$-i | $C_3H_7$-i | $C_5H_9$-cycl. | 4-Cl—$C_6H_4$—O— | |
| 4.36 | $C_3H_7$-i | $C_3H_7$-i | $C(CH_3)_2$—$C_3H_5$-cycl. | 4-Cl—$C_6H_4$—O— | |

TABLE 4-continued

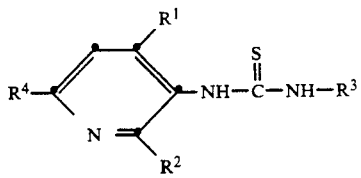

| Comp. No. | R¹ | R² | R³ | R⁴ | m.p. [°C.] |
|---|---|---|---|---|---|
| 4.37 | $C_3H_7$-i | $C_3H_7$-i | $CH(C_3H_7$-i$)_2$ | 4-Cl—$C_6H_4$—O— | |
| 4.38 | $C_3H_7$-i | $C_3H_7$-i | $CH_2$—$C(CH_3)_3$ | 4-Cl—$C_6H_4$—O— | |
| 4.39 | $C_3H_7$-i | $C_3H_7$-i | $C(CH_3)(C_6H_{11}$-cycl.$)_2$ | 4-Cl—$C_6H_4$—O— | |
| 4.40 | $C_3H_7$-i | $C_3H_7$-i | $C_5H_9$-cycl. | 4-F—$C_6H_4$—O— | |
| 4.41 | $C_3H_7$-i | $C_3H_7$-i | $CH(C_3H_9$-i$)_2$ | 4-F—$C_6H_4$—O— | |
| 4.42 | $C_3H_7$-i | $C_3H_7$-i | $CH_2$—$C(CH_3)_3$ | 4-F—$C_6H_4$—O— | |
| 4.43 | $C_3H_7$-i | $C_3H_7$-i | $C_5H_9$-cycl. | 4-$CH_3O$—$C_6H_4$—O— | |
| 4.44 | $C_3H_7$-i | $C_3H_7$-i | $C(CH_3)_2$—$C_2H_5$ | 4-$CH_3O$—$C_6H_4$—O— | |
| 4.45 | $C_3H_7$-i | $C_3H_7$-i | $C_5H_9$-cycl. | 4-$C_4H_9$-t-$C_6H_4$—O— | |
| 4.46 | $C_3H_7$-i | $C_3H_7$-i | $C(CH_3)_2$—$C_2H_5$ | 4-$C_4H_9$-t-$C_6H_4$—O— | |
| 4.47 | $C_3H_7$-i | $C_3H_7$-i | $C_5H_9$-cycl. | 4-$CH_3CO$—$C_6H_4$—O— | |
| 4.48 | $C_3H_7$-i | $C_3H_7$-i | $C(CH_3)_2$—$C_2H_5$ | 4-$CH_3CO$—$C_6H_4$—O— | |
| 4.49 | $C_3H_7$-i | $C_3H_7$-i | $C_4H_9$-t | 4-$CH_3CONH$—$C_6H_4$—O— | 190–192 |
| 4.50 | $C_3H_7$-i | $C_3H_7$-i | $C_4H_9$-t | 4-$C_6H_5CO$—$C_6H_4$—O— | 159–160 |
| 4.51 | $C_3H_7$-i | $C_3H_7$-i | $C_4H_9$-t | 4-$CH_3S$—$C_6H_4$—O— | 156–157 |
| 4.52 | $C_3H_7$-i | $C_3H_7$-i | $C_4H_9$-t | 4-$CH_3$—$C_6H_4$—O— | 158–160 |
| 4.53 | $C_3H_7$-i | $C_3H_7$-i | $C_4H_9$-t | 4-CN—$C_6H_4$—O— | |
| 4.54 | $C_3H_7$-i | $C_3H_7$-i | $C_4H_9$-t | 4-$CF_3CO$—$C_6H_4$—O— | |
| 4.55 | $C_3H_7$-i | $C_3H_7$-i | $C_4H_9$-t | 4-$CH_3OCO$—$C_6H_4$—O— | |
| 4.56 | $C_3H_7$-i | $C_3H_7$-i | $C_4H_9$-t | 4-$CF_3O$—$C_6H_4$—O— | |
| 4.57 | $C_2H_5$ | $C_2H_5$ | $C_4H_9$-t | 4-Cl—$C_6H_4$—O— | 137–140 |
| 4.58 | $C_2H_5$ | $C_2H_5$ | $C_4H_9$-t | 4-F—$C_6H_4$—O— | 132–134 |
| 4.59 | $C_2H_5$ | $C_2H_5$ | $C_4H_9$-t | 2-Cl-4-Cl—$C_6H_3$—O— | |
| 4.60 | $C_2H_5$ | $C_2H_5$ | $C_4H_9$-t | 3-Cl-4-Cl—$C_6H_3$—O— | |
| 4.61 | $C_3H_7$-i | $C_2H_5$ | $C_4H_9$-t | $C_6H_5$—O— | |
| 4.62 | $C_3H_7$-i | $C_2H_5$ | $C_4H_9$-t | 4-Cl—$C_6H_4$—O— | |
| 4.63 | $C_3H_7$-i | $C_2H_5$ | $C_4H_9$-t | 4-$CH_3O$—$C_6H_4$—O— | |
| 4.64 | $C_2H_5$ | $C_3H_7$-i | $C_4H_9$-t | $C_6H_5$—O— | |
| 4.65 | $C_2H_5$ | $C_3H_7$-i | $C_4H_9$-t | 4-Cl—$C_6H_4$—O— | |
| 4.66 | $C_2H_5$ | $C_3H_7$-i | $C_4H_9$-t | 4-$CH_3O$—$C_6H_4$—O— | |
| 4.67 | $C_3H_7$-i | $C_3H_7$-i | $C(CH_3)_2$—$C_6H_{11}$-cycl. | $C_6H_5$—S— | 145–148 |
| 4.68 | $C_3H_7$-i | $C_3H_7$-i | $CH(C_3H_7$-i$)_2$ | $C_6H_5$—S— | 167–174 |

TABLE 5

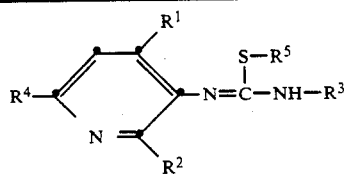

| Comp. No. | R¹ | R² | R³ | R⁴ | R⁵ | m.p. [°C.] |
|---|---|---|---|---|---|---|
| 5.01 | $C_3H_7$-i | $C_3H_7$-i | $C_4H_9$-t | 4-Cl—$C_6H_4$—O— | $CH_3$ | 95–100 |
| 5.02 | $CH_3$ | $CH_3$ | $C_4H_9$-t | $CH_3$ | $CH_3$ | 117–118 |
| 5.03 | $CH_3$ | $CH_3$ | $C_3H_7$-i | $CH_3$ | $CH_3$ | 119–121 |
| 5.04 | $CH_3$ | $CH_3$ | $C_4H_9$-t | $C_6H_5$—O— | $CH_3$ | |
| 5.05 | $CH_3$ | $CH_3$ | $C_4H_9$-t | 4-Cl—$C_6H_4$—O— | $CH_3$ | 118–120 |
| 5.06 | $CH_3$ | $CH_3$ | $C_4H_9$-t | $C_6H_5$—S— | $CH_3$ | |
| 5.07 | $C_3H_7$-i | $C_3H_7$-i | $C_4H_9$-t | H | $CH_3$ | 69–71 |
| 5.08 | $C_3H_7$-i | $C_3H_7$-i | $C_3H_7$-i | H | $CH_3$ | 118–120 |
| 5.09 | $C_3H_7$-i | $C_3H_7$-i | $C_4H_9$-t | Cl | $CH_3$ | 89–92 |
| 5.10 | $C_3H_7$-i | $C_3H_7$-i | $C_3H_7$-i | Cl | $CH_3$ | 89–91 |
| 5.11 | $C_3H_7$-i | $C_3H_7$-i | $C_4H_9$-t | $C_6H_5$—O— | $CH_3$ | 119–122 |
| 5.12 | $C_3H_7$-i | $C_3H_7$-i | $C_3H_9$-i | $C_6H_5$—O— | $CH_3$ | 80–82 |
| 5.13 | $C_3H_7$-i | $C_3H_7$-i | $C_5H_9$-cycl. | $C_6H_5$—O— | $CH_3$ | 80–83 |
| 5.14 | $C_3H_7$-i | $C_3H_7$-i | $C_4H_9$-t | $C_6H_5$—S— | $CH_3$ | 76–80 |
| 5.15 | $C_3H_7$-i | $C_3H_7$-i | $C_3H_7$-i | 4-Cl—$C_6H_9$—O— | $CH_3$ | 90–95 |
| 5.16 | $C_3H_7$-i | $C_3H_7$-i | $C(CH_3)_2$—$C_2H_5$ | 4-Cl—$C_6H_9$—O— | $CH_3$ | 91–93 |
| 5.17 | $C_3H_7$-i | $C_3H_7$-i | $C_4H_9$-t | 4-F—$C_6H_4$—O— | $CH_3$ | 97–100 |
| 5.18 | $C_3H_7$-i | $C_3H_7$-i | $C_3H_7$-i | 4-F—$C_6H_4$—O— | $CH_3$ | 87–90 |
| 5.19 | $C_3H_7$-i | $C_3H_7$-i | $C_4H_9$-t | 2-F—$C_6H_4$—O— | $CH_3$ | 95–97 |
| 5.20 | $C_3H_7$-i | $C_3H_7$-i | $C_4H_9$-t | 2-Cl-4-Cl—$C_6H_3$—O— | $CH_3$ | 97–99 |
| 5.21 | $C_3H_7$-i | $C_3H_7$-i | $C_3H_7$-i | 2-Cl-4-Cl—$C_6H_3$—O— | $CH_3$ | 73–76 |
| 5.22 | $C_3H_7$-i | $C_3H_7$-i | $C_4H_9$-t | 3-Cl-4-Cl—$C_6H_3$—O— | $CH_3$ | 121–123 |
| 5.23 | $C_3H_7$-i | $C_3H_7$-i | $C_3H_7$-i | 3-Cl-4-Cl—$C_6H_3$—O— | $CH_3$ | 80–82 |

TABLE 5-continued

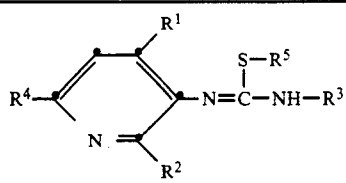

| Comp. No. | R¹ | R² | R³ | R⁴ | R⁵ | m.p. [°C.] |
|---|---|---|---|---|---|---|
| 5.24 | C₃H₇-i | C₃H₇-i | C₄H₉-t | 4-CH₃O—C₆H₄—O— | CH₃ | 78–81 |
| 5.25 | C₃H₇-i | C₃H₇-i | C₃H₇-i | 4-CH₃O—C₆H₄—O— | CH₃ | 107–109 |
| 5.26 | C₃H₇-i | C₃H₇-i | C₄H₉-t | 4-C₄H₉-t-C₆H₄—O— | CH₃ | 110–112 |
| 5.27 | C₃H₇-i | C₃H₇-i | C₃H₇-i | 4-C₄H₉-t-C₆H₄—O— | CH₃ | 80–83 |
| 5.28 | C₃H₇-i | C₃H₇-i | C₄H₉-t | 4-CH₃CO—C₆H₄—O— | CH₃ | 128–130 |
| 5.29 | C₃H₇-i | C₃H₇-i | C₃H₇-i | 4-CH₃CO—C₆H₄—O— | CH₃ | 115–118 |
| 5.30 | C₃H₇-i | C₃H₇-i | C₄H₉-t | 4-(CH₃)₂N—C₆H₄—O— | CH₃ | 104–106 |
| 5.31 | C₃H₇-i | C₃H₇-i | C₃H₇-i | 4-CH₃CONH—C₆H₄—O— | CH₃ | |
| 5.32 | C₃H₇-i | C₃H₇-i | C(CH₃)₂—C₂H₅ | C₆H₅—S— | CH₃ | |
| 5.33 | C₃H₇-i | C₃H₇-i | C₅H₉-cycl. | C₆H₅—S— | CH₃ | |
| 5.34 | C₃H₇-i | C₃H₇-i | CH₂—C(CH₃)₃ | C₆H₅—S— | CH₃ | |
| 5.35 | C₃H₇-i | C₃H₇-i | C₅H₉-cycl. | 4-Cl—C₆H₄—O— | CH₃ | |
| 5.36 | C₃H₇-i | C₃H₇-i | C(CH₃)₂—C₃H₅-cycl. | 4-Cl—C₆H₄—O— | CH₃ | |
| 5.37 | C₃H₇-i | C₃H₇-i | CH(C₃H₇-i)₂ | 4-Cl—C₆H₄—O— | CH₃ | |
| 5.38 | C₃H₇-i | C₃H₇-i | CH₂—C(CH₃)₃ | 4-Cl—C₆H₄—O— | CH₃ | |
| 5.39 | C₃H₇-i | C₃H₇-i | C(CH₃)(C₆H₁₁-cycl.)₂ | 4-Cl—C₆H₄—O— | CH₃ | |
| 5.40 | C₃H₇-i | C₃H₇-i | C₅H₉-cycl. | 4-F—C₆H₄—O— | CH₃ | |
| 5.41 | C₃H₇-i | C₃H₇-i | CH(C₃H₉-i)₂ | 4-F—C₆H₄—O— | CH₃ | |
| 5.42 | C₃H₇-i | C₃H₇-i | CH₂—C(CH₃)₃ | 4-F—C₆H₄—O— | CH₃ | |
| 5.43 | C₃H₇-i | C₃H₇-i | C₅H₉-cycl. | 4-CH₃O—C₆H₄—O— | CH₃ | |
| 5.44 | C₃H₇-i | C₃H₇-i | C(CH₃)₂—C₂H₅ | 4-CH₃O—C₆H₄—O— | CH₃ | |
| 5.45 | C₃H₇-i | C₃H₇-i | C₅H₉-cycl. | 4-C₄H₉-t-C₆H₄—O— | CH₃ | |
| 5.46 | C₃H₇-i | C₃H₇-i | C(CH₃)₂—C₂H₅ | 4-C₄H₉-t-C₆H₄—O— | CH₃ | |
| 5.47 | C₃H₇-i | C₃H₇-i | C₅H₉-cycl. | 4-CH₃CO—C₆H₄—O— | CH₃ | |
| 5.48 | C₃H₇-i | C₃H₇-i | C(CH₃)₂—C₂H₅ | 4-CH₃CO—C₆H₄—O— | CH₃ | |
| 5.49 | C₃H₇-i | C₃H₇-i | C₄H₉-t | 4-CH₃CONH—C₆H₄—O— | CH₃ | 155–158 |
| 5.50 | C₃H₇-i | C₃H₇-i | C₄H₉-t | 4-C₆H₅CO—C₆H₄—O— | CH₃ | 41–42 |
| 5.51 | C₃H₇-i | C₃H₇-i | C₄H₉-t | 4-CH₃S—C₆H₄—O— | CH₃ | 95–96 |
| 5.52 | C₃H₇-i | C₃H₇-i | C₄H₉-t | 4-CH₃—C₆H₄—O— | CH₃ | 94–96 |
| 5.53 | C₃H₇-i | C₃H₇-i | C₄H₉-t | 4-CN—C₆H₄—O— | CH₃ | |
| 5.54 | C₃H₇-i | C₃H₇-i | C₄H₉-t | 4-CF₃CO—C₆H₄—O— | CH₃ | |
| 5.55 | C₃H₇-i | C₃H₇-i | C₄H₉-t | 4-CH₃OCO—C₆H₄—O— | CH₃ | |
| 5.56 | C₃H₇-i | C₃H₇-i | C₄H₉-t | 4-CF₃O—C₆H₄—O— | CH₃ | |
| 5.57 | C₂H₅ | C₂H₅ | C₄H₉-t | 4-Cl—C₆H₄—O— | CH₃ | 90–93 |
| 5.58 | C₂H₅ | C₂H₅ | C₄H₉-t | 4-F—C₆H₄—O— | CH₃ | 94–97 |
| 5.59 | C₂H₅ | C₂H₅ | C₄H₉-t | 2-Cl-4-Cl—C₆H₃—O— | CH₃ | |
| 5.60 | C₂H₅ | C₂H₅ | C₄H₉-t | 3-Cl-4-Cl—C₆H₃—O— | CH₃ | |
| 5.61 | C₃H₇-i | C₂H₅ | C₄H₉-t | C₆H₅—O— | CH₃ | |
| 5.62 | C₃H₇-i | C₂H₅ | C₄H₉-t | 4-Cl—C₆H₄—O— | CH₃ | |
| 5.63 | C₃H₇-i | C₂H₅ | C₄H₉-t | 4-CH₃O—C₆H₄—O— | CH₃ | |
| 5.64 | C₂H₅ | C₃H₇-i | C₄H₉-t | C₆H₅—O— | CH₃ | |
| 5.65 | C₂H₅ | C₃H₇-i | C₄H₉-t | 4-Cl—C₆H₄—O— | CH₃ | |
| 5.66 | C₂H₅ | C₃H₇-i | C₄H₉-t | 4-CH₃O—C₆H₄—O— | CH₃ | |
| 5.67 | C₃H₇-i | C₃H₇-i | C(CH₃)₂—C₆H₁₁-cycl. | C₆H₅—S— | CH₃ | wax |
| 5.68 | C₃H₇-i | C₃H₇-i | CH(C₃H₇-i)₂ | C₆H₅—S— | CH₃ | wax |

TABLE 6

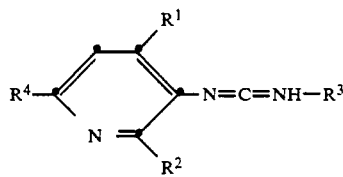

| Comp. No. | R¹ | R² | R³ | R⁴ | phys. data |
|---|---|---|---|---|---|
| 6.01 | C₃H₇-i | C₃H₇-i | C₄H₉-t | 4-Cl—C₆H₄—O— | m.p. 46–55° C. |
| 6.02 | CH₃ | CH₃ | C₄H₉-t | CH₃ | $n_D^{23} = 1.5311$ |
| 6.03 | CH₃ | CH₃ | C₃H₇-i | CH₃ | $n_D^{20} = 1.5410$ |
| 6.04 | CH₃ | CH₃ | C₄H₉-t | C₆H₅—O— | $n_D^{25} = 1.5668$ |
| 6.05 | CH₃ | CH₃ | C₄H₉-t | 4-Cl—C₆H₄—O— | m.p. 59–61° C. |
| 6.06 | CH₃ | CH₃ | C₄H₉-t | C₆H₅—S— | $n_D^{25} = 1.6078$ |
| 6.07 | C₃H₇-i | C₃H₇-i | C₄H₉-t | H | $n_D^{24} = 1.5173$ |
| 6.08 | C₃H₇-i | C₃H₇-i | C₃H₇-i | H | $n_D^{24} = 1.5230$ |
| 6.09 | C₃H₇-i | C₃H₇-i | C₄H₉-t | Cl | $n_D^{23} = 1.5310$ |
| 6.10 | C₃H₇-i | C₃H₇-i | C₃H₇-i | Cl | $n_D^{23} = 1.5363$ |

TABLE 6-continued

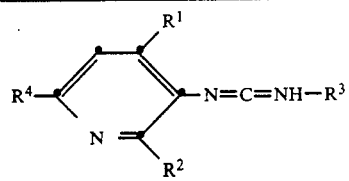

| Comp. No. | $R^1$ | $R^2$ | $R^3$ | $R^4$ | phys. data |
|---|---|---|---|---|---|
| 6.11 | $C_3H_7$-i | $C_3H_7$-i | $C_4H_9$-t | $C_6H_5$—O— | $n_D^{27}$ = 1.5470 |
| 6.12 | $C_3H_7$-i | $C_3H_7$-i | $C_3H_9$-i | $C_6H_5$—O— | $n_D^{25}$ = 1.5485 |
| 6.13 | $C_3H_7$-i | $C_3H_7$-i | $C_5H_9$-cycl. | $C_6H_5$—O— | $n_D^{23}$ = 1.5605 |
| 6.14 | $C_3H_7$-i | $C_3H_7$-i | $C_4H_9$-t | $C_6H_5$—S— | $n_D^{23}$ = 1.5774 |
| 6.15 | $C_3H_7$-i | $C_3H_7$-i | $C_3H_7$-i | 4-Cl—$C_6H_9$—O— | $n_D^{23}$ = 1.5575 |
| 6.16 | $C_3H_7$-i | $C_3H_7$-i | $C(CH_3)_2$—$C_2H_5$ | 4-Cl—$C_6H_9$—O— | $n_D^{22}$ = 1.5515 |
| 6.17 | $C_3H_7$-i | $C_3H_7$-i | $C_4H_9$-t | 4-F—$C_6H_4$—O— | m.p. 56–60° C. |
| 6.18 | $C_3H_7$-i | $C_3H_7$-i | $C_3H_7$-i | 4-F—$C_6H_4$—O— | $n_D^{24}$ = 1.5439 |
| 6.19 | $C_3H_7$-i | $C_3H_7$-i | $C_4H_9$-t | 2-F—$C_6H_4$—O— | $n_D^{25}$ = 1.5379 |
| 6.20 | $C_3H_7$-i | $C_3H_7$-i | $C_4H_9$-t | 2-Cl-4-Cl—$C_6H_3$—O— | $n_D^{23}$ = 1.5525 |
| 6.21 | $C_3H_7$-i | $C_3H_7$-i | $C_3H_7$-i | 2-Cl-4-Cl—$C_6H_3$—O— | $n_D^{23}$ = 1.5595 |
| 6.22 | $C_3H_7$-i | $C_3H_7$-i | $C_4H_9$-t | 3-Cl-4-Cl—$C_6H_3$—O— | m.p. 62–65° C. |
| 6.23 | $C_3H_7$-i | $C_3H_7$-i | $C_3H_7$-i | 3-Cl-4-Cl—$C_6H_3$—O— | $n_D^{24}$ = 1.5645 |
| 6.24 | $C_3H_7$-i | $C_3H_7$-i | $C_4H_9$-t | 4-$CH_3O$—$C_6H_4$—O— | m.p. 37–45° C. |
| 6.25 | $C_3H_7$-i | $C_3H_7$-i | $C_3H_7$-i | 4-$CH_3O$—$C_6H_4$—O— | $n_D^{22}$ 1.5520 |
| 6.26 | $C_3H_7$-i | $C_3H_7$-i | $C_4H_9$-t | 4-$C_4H_9$-t-$C_6H_4$—O— | m.p. 60–63° C. |
| 6.27 | $C_3H_7$-i | $C_3H_7$-i | $C_3H_7$-i | 4-$C_4H_9$-t-$C_6H_4$—O— | $n_D^{23}$ = 1.5445 |
| 6.28 | $C_3H_7$-i | $C_3H_7$-i | $C_4H_9$-t | 4-$CH_3CO$—$C_6H_4$—O— | m.p. 46–51° C. |
| 6.29 | $C_3H_7$-i | $C_3H_7$-i | $C_3H_7$-i | 4-$CH_3CO$—$C_6H_4$—O— | $n_D^{25}$ = 1.5610 |
| 6.30 | $C_3H_7$-i | $C_3H_7$-i | $C_4H_9$-t | 4-$(CH_3)_2N$—$C_6H_4$—O— | $n_D^{23}$ = 1.5629 |
| 6.31 | $C_3H_7$-i | $C_3H_7$-i | $C_3H_7$-i | 4-$CH_3CONH$—$C_6H_4$—O— | |
| 6.32 | $C_3H_7$-i | $C_3H_7$-i | $C(CH_3)_2$—$C_2H_5$ | $C_6H_5$—S— | |
| 6.33 | $C_3H_7$-i | $C_3H_7$-i | $C_5H_9$-cycl. | $C_6H_5$—S— | |
| 6.34 | $C_3H_7$-i | $C_3H_7$-i | $CH_2$—$C(CH_3)_3$ | $C_6H_5$—S— | |
| 6.35 | $C_3H_7$-i | $C_3H_7$-i | $C_5H_9$-cycl. | 4-Cl—$C_6H_4$—O— | |
| 6.36 | $C_3H_7$-i | $C_3H_7$-i | $C(CH_3)_2$—$C_3H_5$-cycl. | 4-Cl—$C_6H_4$—O— | |
| 6.37 | $C_3H_7$-i | $C_3H_7$-i | $CH(C_3H_7$-i$)_2$ | 4-Cl—$C_6H_4$—O— | |
| 6.38 | $C_3H_7$-i | $C_3H_7$-i | $CH_2$—$C(CH_3)_3$ | 4-Cl—$C_6H_4$—O— | |
| 6.39 | $C_3H_7$-i | $C_3H_7$-i | $C(CH_3)(C_6H_{11}$-cycl.$)_2$ | 4-Cl—$C_6H_4$—O— | |
| 6.40 | $C_3H_7$-i | $C_3H_7$-i | $C_5H_9$-cycl. | 4-F—$C_6H_4$—O— | |
| 6.41 | $C_3H_7$-i | $C_3H_7$-i | $CH(C_3H_9$-i$)_2$ | 4-F—$C_6H_4$—O— | |
| 6.42 | $C_3H_7$-i | $C_3H_7$-i | $CH_2$—$C(CH_3)_3$ | 4-F—$C_6H_4$—O— | |
| 6.43 | $C_3H_7$-i | $C_3H_7$-i | $C_5H_9$-cycl. | 4-$CH_3O$—$C_6H_4$—O— | |
| 6.44 | $C_3H_7$-i | $C_3H_7$-i | $C(CH_3)_2$—$C_2H_5$ | 4-$CH_3O$—$C_6H_4$—O— | |
| 6.45 | $C_3H_7$-i | $C_3H_7$-i | $C_5H_9$-cycl. | 4-$C_4H_9$-t-$C_6H_4$—O— | |
| 6.46 | $C_3H_7$-i | $C_3H_7$-i | $C(CH_3)_2$—$C_2H_5$ | 4-$C_4H_9$-t-$C_6H_4$—O— | |
| 6.47 | $C_3H_7$-i | $C_3H_7$-i | $C_5H_9$-cycl. | 4-$CH_3CO$—$C_6H_4$—O— | |
| 6.48 | $C_3H_7$-i | $C_3H_7$-i | $C(CH_3)_2$—$C_2H_5$ | 4-$CH_3CO$—$C_6H_4$—O— | |
| 6.49 | $C_3H_7$-i | $C_3H_7$-i | $C_4H_9$-t | 4-$CH_3CONH$—$C_6H_4$—O— | m.p. 152–154° C. |
| 6.50 | $C_3H_7$-i | $C_3H_7$-i | $C_4H_9$-t | 4-$C_6H_5CO$—$C_6H_4$—O— | m.p. 105–108° C. |
| 6.51 | $C_3H_7$-i | $C_3H_7$-i | $C_4H_9$-t | 4-$CH_3S$—$C_6H_4$—O— | $n_D^{24}$ = 1.5721 |
| 6.52 | $C_3H_7$-i | $C_3H_7$-i | $C_4H_9$-t | 4-$CH_3$—$C_6H_4$—O— | m.p. 46–47° C. |
| 6.53 | $C_3H_7$-i | $C_3H_7$-i | $C_4H_9$-t | 4-$CN$—$C_6H_4$—O— | |
| 6.54 | $C_3H_7$-i | $C_3H_7$-i | $C_4H_9$-t | 4-$CF_3CO$—$C_6H_4$—O— | |
| 6.55 | $C_3H_7$-i | $C_3H_7$-i | $C_4H_9$-t | 4-$CH_3OCO$—$C_6H_4$—O— | |
| 6.56 | $C_3H_7$-i | $C_3H_7$-i | $C_4H_9$-t | 4-$CF_3O$—$C_6H_4$—O— | |
| 6.57 | $C_2H_5$ | $C_2H_5$ | $C_4H_9$-t | 4-Cl—$C_6H_4$—O— | $n_D^{21}$ = 1.5676 |
| 6.58 | $C_2H_5$ | $C_3H_5$ | $C_4H_9$-t | 4-F—$C_6H_4$—O— | $n_D^{21}$ = 1.5504 |
| 6.59 | $C_2H_5$ | $C_3H_5$ | $C_4H_9$-t | 2-Cl-4-Cl—$C_6H_3$—O— | |
| 6.60 | $C_2H_5$ | $C_3H_5$ | $C_4H_9$-t | 3-Cl-4-Cl—$C_6H_3$—O— | |
| 6.61 | $C_3H_7$-i | $C_2H_5$ | $C_4H_9$-t | $C_6H_5$—O— | |
| 6.62 | $C_3H_7$-i | $C_2H_5$ | $C_4H_9$-t | 4-Cl—$C_6H_4$—O— | |
| 6.63 | $C_3H_7$-i | $C_2H_5$ | $C_4H_9$-t | 4-$CH_3O$—$C_6H_4$—O— | |
| 6.64 | $C_2H_5$ | $C_3H_7$-i | $C_4H_9$-t | $C_6H_5$—O— | |
| 6.65 | $C_2H_5$ | $C_3H_7$-i | $C_4H_9$-t | 4-Cl—$C_6H_4$—O— | |
| 6.66 | $C_2H_5$ | $C_3H_7$-i | $C_4H_9$-t | 4-$CH_3O$—$C_6H_4$—O— | |
| 6.67 | $C_3H_7$-i | $C_3H_7$-i | $C(CH_3)_2$—$C_6H_{11}$-cycl. | $C_6H_5$—S— | $n_D^{23}$ = 1.5821 |
| 6.68 | $C_3H_7$-i | $C_3H_7$-i | $CH(C_3H_7$-i$)_2$ | $C_6H_5$—S— | $n_D^{24}$ = 1.5720 |

Formulation Examples (throughout, percentages are by weight)

| Example F1: Emulsifiable concentrates | a) | b) |
|---|---|---|
| compound No. 4.01 or 6.01 | 10% | 25% |
| calcium dodecylbenzenesulfonate | — | 5% |
| castor oil polyethylene glycol | 25% | 5% |

-continued

| Example F1: Emulsifiable concentrates | a) | b) |
|---|---|---|
| ether (36 moles of ethylene oxide) | | |
| cyclohexanone | — | 40% |
| butanol | 15% | — |
| xylene mixture | — | 25% |

| Example F1: Emulsifiable concentrates | | |
|---|---|---|
| | a) | b) |
| ethyl acetate | 50% | — |

Emulsions of any desired concentration can be produced from such concentrates by dilution with water.

| Example F2: Solutions | | |
|---|---|---|
| | a) | b) |
| compound No. 4.01 | 10% | 5% |
| polyethylene glycol (mol. wt. 400) | 70% | — |
| N-methyl-2-pyrrolidone | 20% | 20% |
| epoxidised coconut oil | — | 1% |
| petroleum fraction (boiling range 160–190° C.) | — | 74% |

These solutions are suitable for application in the form of micro-drops.

| Example F3: Granulates | | |
|---|---|---|
| | a) | b) |
| compound No. 4.01 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

Example F4: Extruder granulate
  compound No. 5.01: 10%
  sodium lignosulfonate: 2%
  carboxymethylcellulose: 1%
  kaolin: 87%

The active ingredient is mixed and ground with the adjuvants, and the mixture is subsequently moistened with water. The mixture is extruded and then dried in a stream of air.

Example F5: Coated granulate
  compound No. 4.01: 3%
  polyethylene glycol (mol. wt. 200): 3%
  kaolin: 94%

The finely ground active ingredient is uniformly applied, in a mixer, to the kaolin moistened with polyethylene glycol. Non-dusty coated granulates are obtained in this manner.

| Example F6: Dusts | | | | |
|---|---|---|---|---|
| | a) | b) | c) | d) |
| compound No. 5.01 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by homogeneously mixing the carriers with the active ingredient and where appropriate grinding the mixture in a suitable mill.

| Example F7: Wettable powders | | | |
|---|---|---|---|
| | a) | b) | c) |
| compound No. 6.01 | 20% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is ground in a suitable mill, affording wettable powders which can be diluted with water to give suspensions of the desired concentration.

Example F8: Suspension concentrate
  compound No. 6.01: 40%
  ethylene glycol: 10%
  nonylphenol polyethylene glycol ether (15 moles of ethylene oxide): 6%
  sodium lignosulfonate: 10%
  carboxymethylcellulose: 1%
  37% aqueous formaldehyde solution: 0.2%
  silicone oil in the form of a 75% aqueous emulsion: 0.8%
  water: 32%

The finely ground active ingredient is homogeneously mixed with the adjuvants, giving a suspension concentrate from which suspensions of any desired concentration can be obtained by dilution with water.

BIOLOGICAL EXAMPLES

EXAMPLE B1

Action against Boophilus microplus

Fully replete adult female ticks are affixed to a PvC plate and covered with a cottonwool swab. For the treatent, 10 ml of an aqueous test solution containing 125 ppm of the test compound are poured over the test organisms. The cottonwool swab is then removed and the ticks are incubated for 4 weeks for oviposition. The activity against Boophilus microplus is demonstrated by death or sterility of the females or, in the case of eggs, by ovicidal action.

The compounds according to Tables 4, 5 and 6 exhibit a good activity against Boophilus microplus in this test. In particular, compounds 4.01, 4,11, 4.16, 4.51, 4.52, 5.01, 5.12, 5.13, 5.15, 5.16, 5.20, 5.22, 5.23, 5.50, 5.51, 5.52, 6.01, 6.07, 6.11, 6.12, 6.13, 6.15, 6.21, 6.22, 6.23, 6.24, 6.26, 6.30, 6.50, 6.51 and 6.52 are more than 80% effective.

EXAMPLE B2

Action against Diabrotica balteata larvae

Maize seedlings are sprayed with an aqueous emulsion spray formulation containing 400 ppm of the active ingredient. When the spray coating has dried, the maize seedlings are each populated with 10 larvae of Diabrotica balteata in the $L_2$ stage and placed in a plastics container. Evaluation is carried out six days later. The percentage reduction in population (% effect) is ascertained by comparing the number of dead larvae on the treated plants with the number of dead larvae on the untreated plants.

Compounds from Tables 4, 5 and 6 exhibit a good activity against Diabrotica balteata in this test. In particular, compounds 4.11, 4.20, 4.22, 4.24, 5.01, 5.11, 5.12, 5.15, 5.25 and 5.27 are more than 80% effective.

EXAMPLE B3

Action against Tetranychus urticae

Young bean plants are populated with a mixed population of Tetranychus urticae and sprayed 1 day later with an aqueous emulsion spray formulation containing 400 ppm of the active ingredient. The plants are then incubated for 6 days at 25° C. and subsequently evaluated. The percentage reduction in population (% effect) is ascertained by comparing the number of dead eggs, larvae and adults on the treated plants with that on the untreated plants.

Compounds from Table 4, 5 and 6 exhibit a good activity against Tetranychus urticae in this test. In particular, compounds 4.01, 4.04, 4.12, 4.20, 4.23, 4.24, 4.27, 4.50, 4.51, 4.52, 5.11, 5.13, 5.23, 5.24, 5.50, 5.51, 5.52, 6.06, 6.09, 6.15, 6.23, 6.29, 6.50, 6.51 and 6.52 are more than 80% effective.

EXAMPLE B4

Action against Spodoptera littoralis caterpillars

Young soybean plants are sprayed with an aqueous emulsion spray formulation containing 400 ppm of the active ingredient. When the spray coating has dried, the soybean plants are each populated with 10 caterpillars of Spodoptera littoralis in the L: stage and placed in a plastics container. The evaluation is carried out 3 days later. The percentage reduction in population and the percentage reduction in feeding damage (% effect) are ascertained by comparing the number of dead caterpillars and the feeding damage, respectively, on the treated and untreated plants.

Compounds from Tables 4, 5 and 6 exhibit a good activity against Spodoptera littoralis in this test. In particular, compounds 4.01, 4.11, 4.17, 4.21, 4.26, 4.50, 4.51, 5.09, 5.15, 5.16, 5.18, 5.22, 5.26, 5.51, 5.52, 6.01, 6.09, 6.12, 6.17, 6.21, 6.22, 6.24, 6.26, 6.30, 6.50, 6.51 and 6.52 are more than 80% effective.

EXAMPLE B5

Action against Anthonomus grandis adults

Young cotton plants are sprayed with an aqueous emulsion spray formulation containing 400 ppm of the active ingredient. When the spray coating has dried. the cotton plants are each populated with 10 Anthonomus grandis adults and placed in a plastics container. The evaluation is carried out 3 days later. The percentage reduction in population and the percentage reduction in feeding damage (% effect) are ascertained by comparing the number of dead beetles and the feeding damage, respectively, on the treated and untreated plants.

Compounds from Tables 4, 5 and 6 exhibit a good activity against Anthonomus grandis in this test. In particular, compounds 4.11, 5.01, 5.11, 5.17, 5.22 and 5.23 are more than 80% effective.

EXAMPLE B6

Action against Aphis craccivora

Pea seedlings are infested with Aphis craccivora and then sprayed with a spray formulation containing 400 ppm of the active ingredient and incubated at 20° C. The evaluation is carried out 3 and 6 days later. The percentage reduction in population (% effect) is ascertained by comparing the number of dead aphids on the treated plants with the number on the untreated plants.

Compounds from Tables 4, 5 and 6 exhibit a good activity against Aphis craccivora in this test. In particular, compounds 4.11, 5.01, 5.15, 5.16, 6.01, 6.09, 6.11, 6.12, 6.13, 6.16, 6.17, 6.20, 6.22, 6.24, 6.26, 6.28 and 6.30 are more than 80% effective.

EXAMPLE B7

Action against Myzus persicae

Pea seedlings are infested with Myzus persicae and then sprayed with a spray formulation containing 400 ppm of the active ingredient and incubated at 20° C. The evaluation is carried out 3 and 6 days later. The percentage reduction in population (% effect) is ascertained by comparing the number of dead aphids on the treated plants with that on the untreated plants.

Compounds from Tables 4, 5 and 6 exhibit a good activity against Myzus persicae in this test. In particular, compounds 6.09, 6.12 and 6.13 are more than 80% effective.

EXAMPLE B8

Systemic action against Myzus persicae

Pea seedlings are infested with Myzus persicae and the roots are then placed in a spray formulation containing 400 ppm of the active ingredient and the plants are incubated at 20° C. The evaluation is carried out 3 and 6 days later. The percentage reduction in population (% effect) is ascertained by comparing the number of dead aphids on the treated plants with that on the untreated plants.

Compounds from Tables 4, 5 and 6 exhibit a good activity against Myzus persicae in this test. In particular, compounds 4.11, 6.01, 6.09, 6.11, 6.12, 6.13, 6.16, 6.17, 6.24, 6.26, 6.28 and 6.30 are more than 80% effective.

EXAMPLE B9

Action against Musca domestica

A sugar cube is so moistened with a solution of the test substance that the concentration of active ingredient in the sugar after drying is 500 ppm. This treated cube is placed with a wet cottonwool swab on a dish and covered with a beaker glass. 10 adult 1-week-old and OP-resistant flies are left under the beaker glass at 25° C. and 50% humidity. 24 hours later the insecticidal activity is ascertained by determining the mortality rate.

Compounds from Tables 4, 5 and 6 exhibit a good activity against Musca domestica in this test. In particular, compounds 5.01, 6.01 and 6.07 are more than 80% effective.

EXAMPLE B10

Action against Nilaparvata lugens

Rice plants are treated with an aqueous emulsion spray formulation containing 400 ppm of the active ingredient. When the spray coating has dried, the rice plants are each populated with cicada larvae in the $L_2$ and $L_3$ stage. The evaluation is carried out 21 days later. The percentage reduction in population (% effect) is ascertained by comparing the number of surviving cicadas on the treated plants with the number on the untreated plants.

Compounds from Tables 4, 5 and 6 exhibit a good activity against Nilaparvata lugens in this test. In particular, compounds 4.11, 5.09, 5.11, 5.12, 6.01, 6.09, 6.11, 6.12, 6.16, 6.20, 6.21 and 6.22 are more than 80 effective.

EXAMPLE B11

Systemic action against Nilaparvata lugens

Pots containing rice plants are each placed in an aqueous emulsion-solution containing 400 ppm of the active ingredient. The rice plants are then populated with larvae in the $L_2$ and $L_3$ stage. The evaluation is carried out 6 days later. The percentage reduction in population (% effect) is ascertained by comparing the number of cicadas on the treated plants with the number on the untreated plants.

Compounds from Tables 4, 5 and 6 exhibit a good activity against Nilaparvata lugens in this test. In particular, compounds 5.09, 5.11, 5.15, 5.17, 6.09, 6.10, 6.11, 6.16, 6.17, 6.20, 6.22, 6.24 and 6.26 are more than 80% effective.

EXAMPLE B12

Action against Tetranychus urticae

Young bean plants are populated with Tetranychus urticae females which are removed again after 24 hours. The plants populated with eggs are sprayed with an aqueous emulsion spray formulation containing 400 ppm of the active ingredient. The plants are then incubated for 6 days at 25° C. and subsequently evaluated. The percentage reduction in population (% effect) is ascertained by comparing the number of dead eggs, larvae and adults on the treated plants with that on the untreated plants.

Compounds from Tables 4, 5 and 6 exhibit a good activity against Tetranychus urticae in this test. In particular, compounds 4.11, 4.16, 4.18, 4.22, 4.26, 4.50, 4.51, 4.52, 5.15, 5.18, 5.21, 5.51, 6.13, 6.16, 6.22, 6.24, 6.30, 6.50, 6.51 and 6.52 are more than 80% effective.

EXAMPLE B13

Action against Panonychus ulmi (OP- and Carb.-resistant)

Apple seedlings are populated with adult females of Panonychus ulmi. Seven days later the infested plants are sprayed to drip point with an aqueous emulsion spray formulation containing 400 ppm of the test compound and cultivated in a greenhouse. The evaluation is carried out 14 days later. The percentage reduction in population (% effect) is ascertained by comparing the number of dead spider mites on the treated plants with that on the untreated plants.

Compounds from Tables 4, 5 and 6 exhibit a good activity against Panonychus ulmi in this test. In particular, compounds 4.16, 4.24, 4.26, 4.52, 6.28 and 6.50 are more than 80% effective.

EXAMPLE B14

Action against Dermanyssus gallinae 2 to 3 ml of a solution containing 10 ppm of active ingredient and approximately 200 mites at different stages of development are placed in a glass container open at the top. The container is then closed with a cottonwool swab, shaken for 10 minutes until the mites are completely wet, and then briefly inverted so that the remainder of the test solution can be absorbed by the swab. The mortality is ascertained 3 days later by counting the number of dead mites.

Compounds from Tables 4, 5 and 6 exhibit a good activity against Dermanyssus gallinae in this test. In particular, compounds 4.07, 5.07, 5.16, 5.51, 6.07, 6.11 and 6.52 are more than 80% effective.

EXAMPLE B15

Action against Blattella germanica

That amount of a 0.1% solution of the active ingredient in acetone sufficient to provide an application rate of 2 g/m² is placed in a Petri dish. When the solvent has evaporated, 10 Blattella germanica nymphs (final nymph stage) are added to the prepared dish and exposed for 2 hours to the action of the test compound. The nymphs are then narcotised with $CO_2$, placed in a fresh Petri dish and kept in the dark at 25° C. and 50 to 70% humidity. After 48 hours, the insecticidal activity is ascertained by determining the mortality rate.

Compounds from Tables 4, 5 and 6 exhibit a good activity against Blattella germanica in this test. In particular, compounds 6.01, 6.12, 6.13 and 6.15 are more than 80% effective.

What is claimed is:

1. A 3-Amino-2,4-dialkylpyridine derivative of formula I

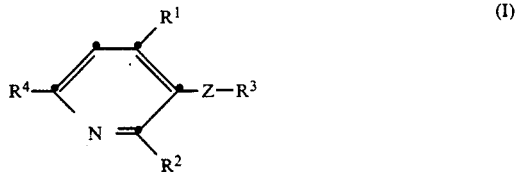

in which $R^1$ and $R^2$ are each independently $C_1$-$C_6$alkyl, $R^3$ is $C_1$-$C_{12}$alkyl, $C_3$-$C_6$cycloalkyl, $C_1$-$C_4$alkyl substituted by $C_3$-$C_6$cycloalkyl, or $C_3$-$C_6$cycloalkyl substituted by $C_1$-$C_4$alkyl, $R^4$ is hydrogen, halogen, $C_1$-$C_6$alkyl, phenoxy, or phenoxy that is mono- or di-substituted by halogen, $C_1$-$C_4$alkyl, $C_1$-$C_4$alkoxy, $C_1$-$C_4$alkylthio, $C_1$-$C_4$alkylamino, di-$C_1$-$C_4$alkylamino, $C_1$-$C_4$alkylcarbonylamino, $C_1$-$C_4$alkylcarbonyl, benzoyl, nitro, cyan, $C_1$-$C_4$alkoxycarbonyl, $C_1$-$C_4$haloalkyl or by $C_1$-$C_4$haloalkoxy, and Z is a bridge member -NH-CS-NH-, -N=C(SR⁵)-NH- or -N=C=N- wherein $R^5$ is $C_1$-$C_6$alkyl or $C_3$-$C_5$alkenyl.

2. A compound according to claim 1, wherein $R^1$ and $R^2$ have the same meaning.

3. A compound according to claim 1, wherein $R^1$ and $R^2$ are isopropyl.

4. A compound according to claim 1, wherein $R^3$ is branched $C_3$-$C_5$alkyl.

5. A compound according to claim 4, wherein $R^3$ is isopropyl, tert.-butyl or 1,1-dimethylpropyl.

6. A compound according to claim 1, wherein $R^4$ is phenoxy substituted by halogen, by $C_1$-$C_4$alkyl or by $C_1$-$C_4$alkoxy.

7. A compound according to claim 1, wherein $R^4$ is chlorophenoxy, fluorophenoxy, methoxyphenoxy, tert.-butylphenoxy or dichlorophenoxy.

8. A compound according to claim 1, wherein $R^1$ and $R^2$ have the same meaning, $R^3$ is branched $C_3$-$C_5$alkyl and $R^4$ is phenoxy substituted by halogen, by $C_1$-$C_4$alkyl, by di-$C_1$-$C_4$alkylamino or by $C_1$-$C_4$alkoxy.

9. A compound according to claim 1, wherein $R^1$ and $R^2$ are isopropyl, $R^3$ is isopropyl, tert.-butyl or 1,1-dimethylpropyl and $R^4$ is chlorophenoxy, fluorophenoxy, dichlorophenoxy, methoxyphenoxy or tert.-butylphenoxy.

10. A compound according to claim 1, wherein $R^5$ is $C_1$–$C_4$alkyl.

11. A compound according to claim 1 selected from the group consisting of 1-tert.butyl-3-[2,4-diisopropyl-6-(4-chlorophenoxy)-pyrid-3-yl]-thiourea, 1-tert.-butyl-3-[2,4-diisopropyl-6-(4-chlorophenoxy)-pyrid-3-yl]-S-methyl-isothiourea, 1-tert.-butyl-3-[2,4-diisopropyl-6-(4-chlorophenoxy)pyrid-3-yl]-carbodiimide, 1-tert.-butyl-3-[2,4-diisopropyl-6-(4-methoxyphenoxy)-pyrid-3-yl]-thiourea, 1-tert.-butyl-3-[2,4-diisopropyl-6-(4-methoxyphenoxy)-pyrid-3-yl]-S-methyl-isothiourea and 1-tert.-butyl-3-[2,4-diisopropyl-6-(4-methoxyphenoxy)-pyrid-3-yl]-carbodiimide.

12. A method of controlling insects and arachnids that are harmful to animals and plants which comprises treating the pests or said locus thereof with an effective amount of a compound of formula I according to claim 1.

13. A composition that comprises as active component at least an insecticidally and arachinidicidally effective amount of a compound according to claim 1 and a carrier therefor.

* * * * *